(12) United States Patent
Lin

(10) Patent No.: US 9,572,832 B2
(45) Date of Patent: Feb. 21, 2017

(54) COMPOUND OF GLYCOSAMINOGLYCAN AND ITS FABRICATION METHOD AS WELL AS APPLICATION

(71) Applicant: HOLY STONE HEALTHCARE CO., LTD., Taipei (TW)

(72) Inventor: Hua-Yang Lin, Taipei (TW)

(73) Assignee: HOLY STONE HEALTHCARE CO., LTD., Taipei (TW)

( * ) Notice: Subject to any disclaimer, the term of this patent is extended or adjusted under 35 U.S.C. 154(b) by 133 days.

(21) Appl. No.: 14/308,972

(22) Filed: Jun. 19, 2014

(65) Prior Publication Data
US 2015/0065446 A1 Mar. 5, 2015

Related U.S. Application Data

(60) Provisional application No. 61/871,352, filed on Aug. 29, 2013.

(51) Int. Cl.
| | |
|---|---|
| *A61K 31/728* | (2006.01) |
| *A61K 31/145* | (2006.01) |
| *A61K 31/445* | (2006.01) |
| *A61K 31/454* | (2006.01) |
| *A61K 47/36* | (2006.01) |
| *A61K 47/48* | (2006.01) |
| *A61K 31/415* | (2006.01) |
| *A61K 31/7068* | (2006.01) |
| *A61K 31/573* | (2006.01) |

(52) U.S. Cl.
CPC .......... *A61K 31/728* (2013.01); *A61K 31/145* (2013.01); *A61K 31/415* (2013.01); *A61K 31/445* (2013.01); *A61K 31/454* (2013.01); *A61K 31/573* (2013.01); *A61K 31/7068* (2013.01); *A61K 47/4823* (2013.01); *A61K 47/48092* (2013.01)

(58) Field of Classification Search
None
See application file for complete search history.

(56) References Cited

PUBLICATIONS

Safran, H. et al., Journal of Clinical Oncology, 2010 ASCO Annual Meeting Abstracts, "Lenalidomide for advanced hepatocellular cancer (HCC) in patients progressing on or intolerant to sorafenib", May 20 Supplement, vol. 28, No. 15: 4159.*
Zhang, Li et al., International Journal of Pharmaceutics, "Glycyrrhetinic acid-graft-hyaluronic acid conjugate as a carrier for synergistic targeted delivery of antitumor drugs", published online Oct. 2012, vol. 441, pp. 654-664.*
Ursula Gunthert et al, A New Variant of Glycoprotein CD44 Confers Metastatic Potential to Rat Carcinoma Cells, Cell, vol. 65, 13-24, Apr. 5, 1991.
F. Reihani-Sabet et al, Effects of Inflammation and H. Pylori Infection on Expression of CD44 Variant Exons in Gastric Tissue, Journal of Sciences, Islamic Republic of Iran 14(1): 11-16 (2003) National Center for Scientific Research, ISSN 1016-1104.
Rom E. Eliaz et al, Liposome-encapsulated Doxorubicin Targeted to CD44: A Strategy to Kill CD44-overexpressing Tumor Cells, Cancer Research 61, 2592-2601, Mar. 15, 2001.
Robert S. Sandler, M.D., M.P.H. et al, A Randomized Trial of Aspirin to Prevent Colorectal Adenomas in Patients with Previous Colorectal Cancer, The New England Journal of Medicine, Mar. 6, 2003, V. 308 No. 10, pp. 883-890.
R. Yamazaki et al., Selective cyclooxygenase-2 inhibitors show a differential ability to inhibit proliferation and induce apoptosis of colon adenocarcinoma cells, FEBS Letters 531 (2002) 278-284.
Andrew J. Dannenberg et al, Targeting cyclooxygenase-2 in human neoplasia: Rationale and promise, Cancer Cell : Dec. 2003 • vol. 4, pp. 431-436.
Alane T.Koki, PhD et al, Celecoxib: A Specific COX-2 Inhibitor With Anticancer Properties, Cancer Control, Mar./Apr. 2002, vol. 9, No. 2 Supplement, pp. 28-35.
Yan-Jie Zhang, MD, PhD et al, mTOR Signaling is Involved in Indomethacin and Nimesulide Suppression of Colorectal Cancer Cell Growth via a COX-2 Independent Pathway, Ann Surg Oncol (2011) 18:580-588 DOI 10.1245/s10434-010-1268-9.
Venumadhav Kotla et al, Mechanism of action of lenalidomide in hematological malignancies, Journal of Hematology & Oncology, 2009, 2:36, Aug. 12, 2009.
Jacob Sheskin, M.D., The Treatment of Lepra Reaction in Lepromatous Leprosy, International Journal of Dermatolocy Jul.-Aug. 1980 vol. 19, pp. 318-322.
E Atra et al, Treatment of the cutaneous lesions of systemic lupus erythematosus with thalidomide, Clinical and experimental rheumatology (Impact Factor: 2.66). Jan. 1993; 11(5):487-93 Abstract.
Dominique Verhelle et al, Lenalidomide and CC-4047 Inhibit the Proliferation of Malignant B Cells while Expanding Normal CD34+ Progenitor Cells, Cancer Res 2007; 67: (2). Jan. 15, 2007, pp. 746-755.
D Gupta et al, Adherence of multiple myeloma cells to bone marrow stromal cells upregulates vascular endothelial growth factor secretion: therapeutic applications, Leukemia (2001) 15, pp. 1950-1961.

* cited by examiner

*Primary Examiner* — Shaojia Anna Jiang
*Assistant Examiner* — Bahar Craigo
(74) *Attorney, Agent, or Firm* — patenttm.us

(57) ABSTRACT

The present invention is related to a compound conjugating a drug with a glycosaminoglycan, such as hyaluronic acid (HA), where the drug is useful for the treatment of diseases such as inflammation, auto-immune disease, allergy, infection and preferably cancer. The conjugated compound of the present invention can increase the concentration of drug at the specific site of disease by an interaction of the glycosaminoglycan used as target drug delivery carrier and the CD44 cell surface receptor, then enhancing the therapeutic efficacy and reducing the systemic side effect of the site-delivered drug.

5 Claims, 17 Drawing Sheets

HA-NiNH$_2$

COMPOUND OF GLYCOSAMINOGLYCAN AND ITS FABRICATION METHOD AS WELL AS APPLICATION

CROSS REFERENCE

This application claims priority to U.S. Provisional Patent Application Ser. No. 61/871,352, filed on Aug. 29, 2013, the content of which is hereby incorporated by reference in its entirety.

BACKGROUND OF THE INVENTION

1. Field of the Invention

The present invention relates to a compound consisting of a glycosaminoglycan conjugated with a drug and to a preparation method thereof as well.

2. Description of the Prior Arts

The extracellular matrix (ECM) is a dynamic assemblage of interacting molecules that regulate cell functions and interactions in response to stimulation. One class of extracellular matrix macromolecules, the glycosaminoglycans, are molecules known to be involved in a wide array of both normal and abnormal biological processes, including cell migration, differentiation, proliferation, immune response and cytoskeletal organization.

Glycosaminoglycans (GAGs) are unbranched chains composed of repeating disaccharide units. These disaccharide units always contain an amino sugar (N-acetylglucosamine or N-acetylgalactosamine), which in most cases is sulfated, with the second sugar usually being an uronic acid (glucuronic or iduronic). GAGs are highly negatively charged because of the presence of carboxyl or sulfate groups on most of their sugar residues. As such they are strongly hydrophilic. GAGs tend to adopt highly extended conformations and form matrices that are space filling and resistant to compressive forces. Four main groups of GAGs have been distinguished by their sugar residues, the type of linkage between these residues, and the number and location of sulfate groups. They include: (1) hyaluronan, (2) chondroitin sulphate and dermatan sulfate, (3) heparan sulfate and heparin, and (4) keratan sulfate.

Hyaluronan (also called hyaluronic acid or hyaluronate or HA) is the simplest of GAGs. It consists of a regular repeating sequence of non-sulfated disaccharide units, specifically N-acetylglucosamine and glucuronic acid. Its molecular weight can range from 400 daltons (the disaccharide) to over millions of daltons. It is found in variable amounts in all tissues, such as the skin, cartilage, and eye, and in most, if not all, fluids in adult animals. It is especially abundant in early embryos. In articular cartilage, HA can form a large aggregate which is important for the function of cartilage. Furthermore, cell motility and immune cell adhesion is mediated by the cell surface receptor RHAMM (Receptor for Hyaluronan-Mediated Motility) and CD44.

HA is synthesized directly at the inner membrane of the cell surface with the growing polymer extruded through the membrane to the outside of the cell as it is being synthesized. Synthesis is mediated by a single protein enzyme, hyaluronan synthetase (HAS). By contrast, other GAGs are synthesized inside the cell in the Golgi apparatus, possibly in association with some core protein, and then released by exocytosis. HA degradation in vertebrate tissues in vivo is mediated by hyaluronidase, and exoglycosidases that remove sugars sequentially. Mammalian-type hyaluronidases have both hydrolytic and transglycosidase activities and can degrade HA and chondroitin. In connective tissue, the water of hydration associated with HA creates spaces between tissues, thus creating an environment conducive to cell movement and proliferation. HA plays a key role in biological phenomena associated with cell motility including rapid development, regeneration, repair, embryogenesis, embryological development, wound healing, angiogenesis, and tumorigenesis.

CD44 (also known as Pgp-1, Hermes-3, HCAM, ECMR III) is a widely expressed glycoprotein with a molecular weight of 85 to 90 kDa. CD44 is a major cell surface receptor for the glycosaminoglycan, hyaluronic acid (HA). CD44 binds HA specifically, although certain chondroitin-sulfate containing proteoglycans may also be recognized. CD44 plays a role in various cellular and physiological functions, including adhesion to and migration on HA, HA degradation and tumor metastasis. CD44 has also been shown to play a role in extracellular matrix binding, cell migration, lymphocyte activation, lymphocyte homing, and proliferation of bronchial smooth muscle cell (Gunthert et al., 1991, *A new variant of glycoprotein CD44 confers metastatic potential to rat carcinoma cells,* 5; 65(1):13-24). The CD44 receptor shows a complex pattern of alternative splicing in its variable region of the extracellular domain. CD44 appears to be a particularly important leukocyte receptor for HA and may therefore have a role in the pathogenesis of asthma. In addition, levels of HA, which were increased during experimental asthma in control mice were markedly attenuated in the antibody-treated mice, supporting a role for CD44 in HA metabolism (specifically in the breakdown of high molecular weight HA to pro-inflammatory low molecular weight forms). This may be particularly important because HA-derived oligosaccharides can bind and activate Toll-like receptor. Clearly, the most impressive aspect of the results is the profound magnitude of the beneficial effects of anti-CD44 treatment.

HA-CD44 interactions may play an important role in development, inflammation, T cell recruitment and activation, lung inflammation, and tumor growth and metastasis. Altered expression of alternatively spliced CD44 transcripts has been found in many cancers, including cancer of the stomach (F Reihani-Sabet et al., 2003, *Effects of Inflammation and H. pylori Infection on Expression of CD44 Variant Exons in Gastric Tissue*, Journal of Sciences, 14:11-16).

Malignant tumor cells could selectively ingest proportionally more of bioconjugates than normal connective tissue or mesenchymal cells due to their overexpression of the CD44 receptor. Several studies have correlated increased HA synthesis and uptake with cancer progression and metastatic potential. Certain tumors, including many that are found in the lung, overexpress the CD44 cell-surface marker. Breast cancer cells are known to have greater uptake of HA than normal tissues, requiring HA for high P-glycoprotein expression, the primary contributor to multi-drug resistance. Furthermore, invasive breast cancer cells overexpress CD44, the primary receptor for HA, and are dependent on high concentrations of CD44-internalized HA for proliferation. Thus, chemotherapeutic drug nanoconjugates with HA may be efficacious against lymphatic metastases. (Eliaz, R. E. et al., 2004, *Liposome-encapsulated doxorubicin targeted to CD44: a strategy to kill CD44-overexpressing tumor cells*, Cancer Res., 61(6):2592-601).

Non-steroidal anti-inflammatory drugs (NSAIDs) and selective inhibitors of cyclooxygenase (COX)-2, are therapeutic groups generally used for the treatment of pain, inflammation and fever. Recently, growing experimental implies that some NSAIDs and the selective COX-2 inhibitors may also have anti-cancer activity by involving in multiple biologic events throughout the tumorigenic process. For example, epidemiological studies have shown that regular use of Aspirin reduces the risk of developing cancer, in particular of the colon (Sandler R S., et al., 2003, *A randomized trial of aspirin to prevent colorectal adenomas in patients with previous colorectal cancer*, New England J. Med., 348:883-890). Otherwise, it is also found that the COX-2 antagonist, such as Celecoxib, Rofecoxib, Nimesulide, meloxicam and Etodolac, can also have anti-cancer activity (Yamazaki R., et al., 2002, *Selective cyclooxygenase-2 inhibitors show a differential ability to inhibit proliferation and induce apoptosis of colon adenocarcinoma cells*, FEBS Lett., 531(2):278-84). Further, COX-2 is chronically overexpressed in many premalignant, malignant, and metastatic human cancers, and levels of overexpression have been shown to significantly correlate to invasiveness, prognosis, and survival in some cancers (Dannenberg A J., et al., 2003, *Targeting cyclooxygenase-2 in human neoplasia: rationale and promise*, Cancer Cell, 4(6):431-6). Maximum efficacy is typically dose-limited by COX-1-related toxicities; however, COX-2 inhibitors have been shown to have tumor suppression effect in several animal models of colon, skin, lung, bladder, and breast cancers (Alane T. Koki, et al., 2002, *Celecoxib: A Specific COX-2 Inhibitor With Anticancer Properties*, Cancer Control, 9(2 Suppl):28-35).

WO94/09811 describes the use of CD44 in treating inflammation or detecting cancer metastasis. The authors show that CD44 is upregulated in inflammatory conditions and CD44 peptides are capable of inhibiting T-cell activation. No data or claims are presented on inhibition of metastasis by CD44 and no claims are made towards use of CD44 for inhibiting tumor growth or angiogenesis. WO 99/45942 discloses the use of HA-binding proteins and peptides, including CD44, to inhibit cancer and angiogenesis-dependent diseases. This patent application uses metastatin, a 38 kDa fragment of the cartilage link protein, as well as a HA-binding peptide derived from this fragment to inhibit pulmonary metastasis of B16 mouse melanoma and Lewis lung carcinoma. In the case of the HA-binding peptide, growth of B16 melanoma on chicken CAM and endothelial cell migration on HA have been inhibited. In both patent applications the use of HA-binding peptides is directly related to their ability to bind hyaluronic acid.

U.S. Pat. No. 8,192,744 shows that soluble recombinant CD44 hyaluronic acid binding domain (CD44HABD) inhibits angiogenesis in vivo in chick and mouse and thereby inhibits human tumor growth of various origins. The invention discloses soluble non glycosylated CD44 recombinant proteins as a novel class of angiogenesis inhibitors based on targeting of vascular cell surface receptor.

Thus, the prior arts, hereinabove cited, disclose the potential use of CD44 and suggest that any effects can be dependent on HA-CD44-interaction. Consequently, all utility ascribed so far to CD44-HA conjugate is directly dependent on their ability to bind hyaluronic acid.

However, some drugs are still not successfully conjugated onto HA and further experiments should be carried out to confirm the potential usefulness of HA as site-delivery carrier of active compound. In particular, the prior art has not shown that the interactions between the surface cell receptor CD44 and a conjugate of HA with an active compound can be profitably exploited for a target delivery of such active compound in diseases characterized by an overexpression of CD44 obtaining an effective therapeutic improvement of the same.

For pathologies, such as for example cancer, in fact, it is still a need felt to have available therapeutic tools balancing an effective cytotoxic effect against the tumoral cells and the cytotoxic effects on the normal cells with a better safety profile.

SUMMARY OF THE INVENTION

The purpose of the present invention is to provide new compound based on the conjugation of HA with active compound suitable for a site delivery of such active compound in diseases overexpressing the surface cell receptor CD44.

The present invention, therefore, provides a compound conjugating glycosaminoglycan with a drug, wherein the drug is used for treating diseases of cancer that are highly related with the expression of CD44.

In a first aspect, it is an object of the invention a compound consisting of a conjugate from a glycosaminoglycan and an active compound, wherein the active compound is conjugated by means of a functional group to a carboxylic group of the glycosaminoglycan, its derivative, or a salt thereof to form a covalent conjugation, and wherein the active compound is selected from a group consisting of Lenalidomide and a COX-2 antagonist.

The glycosaminoglycan of the conjugate according of the present invention is preferably hyaluronic acid.

Furthermore, the glycosaminoglycan conjugate according of the present invention is preferably for use for treating cancer diseases.

Therefore, in a second aspect it is a further object of the invention the use of a compound consisting of a conjugate from a glycosaminoglycan and an active compound, wherein the active compound is conjugated by means of a functional group to a carboxylic group of the glycosaminoglycan, its derivative, or a salt thereof to form a covalent conjugation, and wherein the active compound is selected from a group consisting of Lenalidomide and a COX-2 antagonist for the treatment of cancer and for the preparation of pharmaceutical compositions for said therapeutic treatment.

Yet in a further aspect, it is an object of the present invention the method for preparing a compound consisting of a conjugate from a glycosaminoglycan and an active compound, wherein the active compound is conjugated by means of a functional group to a carboxylic group of the glycosaminoglycan, its derivative, or a salt thereof to form a covalent conjugation, and wherein the active compound is selected from a group consisting of Lenalidomide and a COX-2 antagonist.

BRIEF DESCRIPTION OF THE DRAWINGS

To adequately describe the present invention, references to embodiments thereof are illustrated in the appended drawings. These drawings herewith form a part of the specification. However, the appended drawings are not to be considered limiting in their scope.

FIG. 2 shows the fluorescence results of HA-dye compound working on HCT 15 cell line and HT29 cell line with different time courses, wherein

DETAILED DESCRIPTION OF THE PREFERRED EMBODIMENTS

Other objectives, advantages and novel features of the invention will become more apparent from the following detailed description when taken in conjunction with the accompanying drawings.

In general, a drug orally administered or injected into circulation system must directly arrive at its targeted treatment area, and therefore the drug effect on targeted disease and normal organ is very similar because the concentration and specificity are not so high on the targeted site, limited by safety profile.

In order to improve the therapy efficacy combining the same with good safety profile, one strategy is to modify the drug to be more target-selective to the disease area through a covalent binding the drug with a carrier. This is a need particularly felt in the field of antitumor therapy as previously anticipated.

At this purpose, the inventor has conceived the idea to exploit the interactions between the hyaluronic acid (HA) and its receptor CD44 for a target delivering active substance.

The idea to maintain the relative higher concentration of the drug on the targeted site versus normal tissue or organ has been established by the inventor following long-term study and experiment on HA.

The results, from which the present invention originates, are fully described in the examples and are hereinafter briefly summarized.

Figure 1:
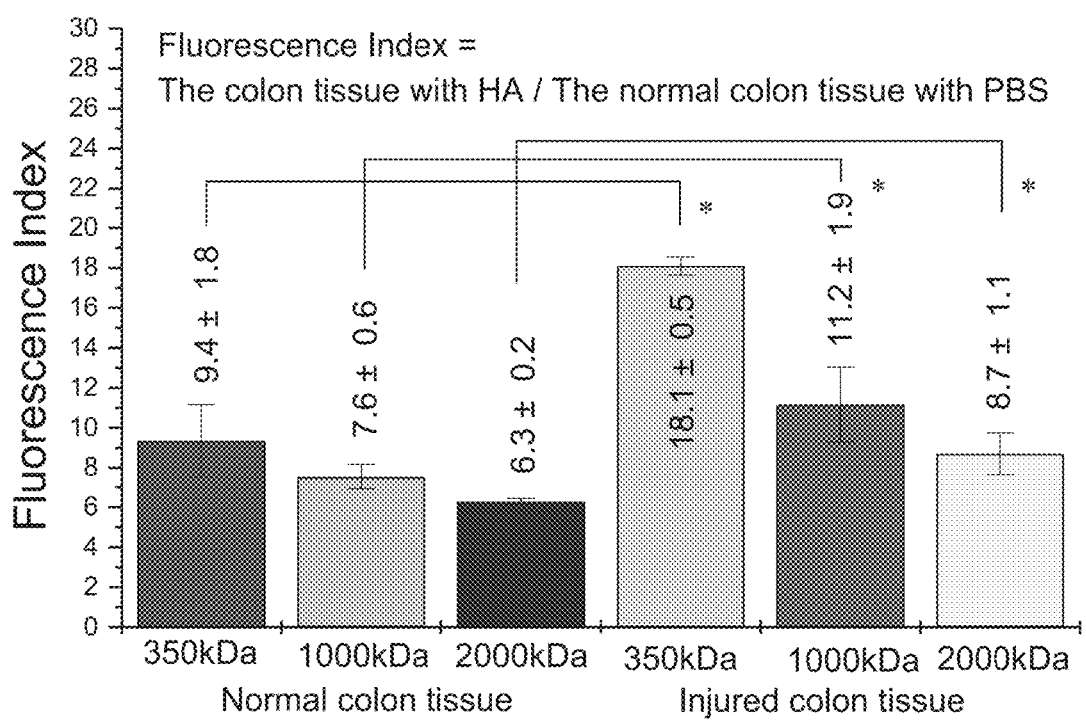
FIG. 1 shows the affinity of HAs by fluorescent index in normal and injured colon tissues.

In fact, the present invention finds support on the result showing that hyaluronic acids having different average molecular weights (MW) have an adhesion index higher in injured tissue than in normal tissue and that the HA with low average molecular weight performs better than the HAs with high average molecular weights. In particular, as shown in FIG. 1, comparing the differences among HAs of three average molecular weights adhered on the injured colon tissues, the fluorescent index of adhesion of 350 KDa HA by the injured colon tissues was higher than the HAs of the other two average molecular weights (2000 KDa=2 MDa and (1000 KDa=1 MDa). Further, the fluorescent index of adhesion of 1 MDa HA by even normal or injured colon tissues was higher than 2 MDa HA. This result confirmed that the HA can more specifically adhere on the inflammation site, which induces the inventor to further invent the present invention and to verify whether this peculiar feature of tissue adhesion of hyaluronic acid, allegedly due to an interaction of HA with its surface cell receptor CD44, can be maintain when this glycosaminoglycan is conjugated with other compounds.

Therefore, the inventor further conjugates a drug with HA in order to verify if HA can be used as a targeted delivery vehicle to conduct the drug onto CD44 abundance site. As aforementioned, when CD44 is overexpressed during the situation of existence of inflammation, infection or a cancer, a related drug can easily arrive at and retain relative high concentration on the targeted site owing to ligand HA attaches onto receptor CD44. In accompany with HA's adherence effect to inflammation site or CD44 abundance site, the conjugated drug should especially aggregate on the targeted part to enhance the therapy efficacy owing to relative higher concentration of the drug on the site, and hence decreasing accordingly the amount of the drug utilized with better safety profile.

Figure 2A:
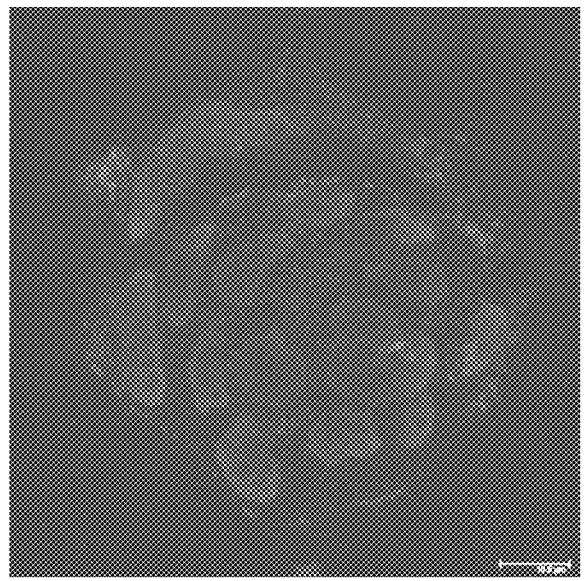
FIG. 2A represents HCT 15 cell line at 6 hours.
Figure 2B:
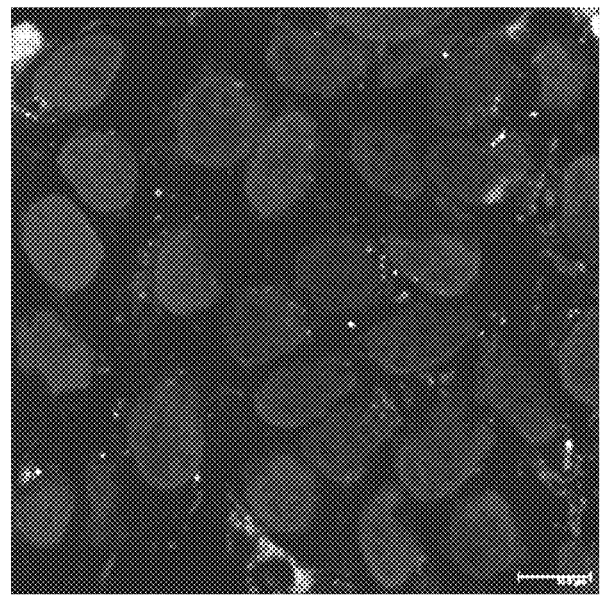
FIG. 2B represents HCT 15 cell line at 12 hours.
Figure 2C:
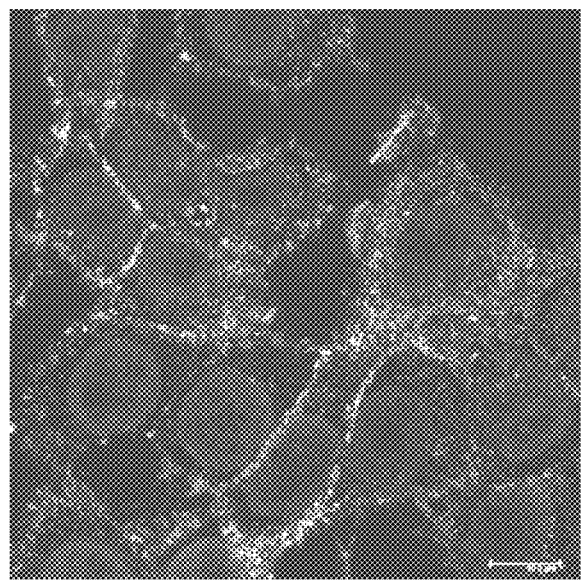
FIG. 2C represents HT29 cell line at 6 hours.
Figure 2D:
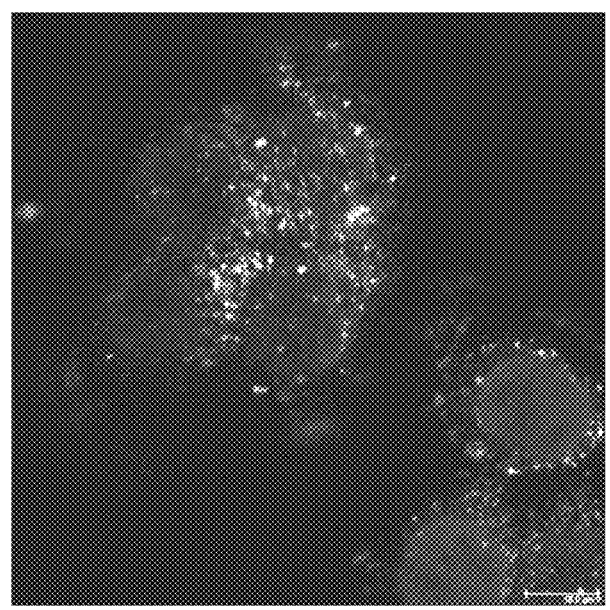
FIG. 2D represents HT29 cell line at 12 hours.

In order to confirm the drug or dye has been successfully conjugated with HA and further confirm the HA attachment effect, the inventor of the present invention conducted an experiment including conjugating dye onto HA (HA-dye) and treating with the cell lines and mice separately. FIG. 2A and FIG. 2B show the experiments at different working times on cell line HCT15 (a colorectal adenocarcinoma with less CD44), and FIG. 2C and FIG. 2D show the experiments at different working times on cell line HT29 (a colorectal adenocarcinoma with rich CD44). The results of HT29 (FIG. 2C and FIG. 2D) show the HA-dye have been successfully conjugated and attached onto CD44 abundant area of HT29 (FIG. 2C), and even enter into HT29 cells (FIG. 2D). That means the idea of the present invention is proper and effective and also means drug or dye can be conjugated to HA and that HA retain its capability to bind CD44.

The attachment condition of free dye and HA-dye on cell lines of HT29 and HCT15 of mice for 4 weeks was conducted. The free dye was injected into the tail vein of the mice. The result showed that the two different CD44 expression cancer cells without any difference in attachment result. The ratio of attachment area of HT29 is 50.15%, whereas HCT15 is 49.86%. However, when the HA conjugated dye was injected into the mice tail vein, the more CD44 expression cancer cell HT 29 showed significant concentration of HA conjugated dye, but the less CD44 expression HCT15 showed very limited result. The ratio of attachment area of HT29 is 74.15%, whereas HCT15 is 25.85%. The result can show that when dye conjugated with HA, the concentration of dye was increased owing to HA attached on CD44 abundant site.

CD44 highly related diseases include cancer, infection and inflammation. In a preferred embodiment of the present invention, for example, cancer includes colon carcinoma, fibrosarcoma, breast cancer, adenocarcinoma, and brain malignant glioma.

In the specification and in the claims the term "drug" or "active compound" or "agent" for used in the present invention may comprise anti-cancer drug. The majority of anti-cancer drugs can be divided into alkylating agents, anti-metabolites, anthracyclines, plant alkaloids, topoisomerase inhibitors, and other anticancer drugs.

In a preferred embodiment, the conjugation of anti-cancer drug includes, but is not limited to, Lenalidomide, Gemcitabine, Celecoxib, and Nimesulide.

Nimesulide is one of the widely used selective COX-2 antagonist which has superior gastrointestinal safety as compared to other NSAIDs. In recent time, Nimesulide was supposed to act as an anti-cancer drug by inducing the expression of p21, a tumor suppressor gene, and inhibit the mammalian target of rapamycin (mTOR)-related pathway, an essential pathway for cell growth, cell proliferation, cell motility, cell survival, protein synthesis, of cancer cells (Zhang Y J., et al., 2011, *mTOR signaling is involved in indomethacin and nimesulide suppression of colorectal cancer cell growth via a COX-2 independent pathway*. Ann Surg Oncol., 18(2):580-8).

Lenalidomide, a 4-amino-glutamyl analogue of thalidomide, are synthetic compounds derived by modifying the chemical structure of thalidomide to improve its potency and reduce its teratogenic and neurologic side effects (V. Kotla, et al., 2009, *Mechanism of action of lenalidomide in hematological malignancies*, Journal of Hematology and Oncology, 2:36). Lenalidomide has been shown anti-angiogenic, anti-tumorigenic, and immunomodulating activity that was realized due to anecdotal immunomodulatory activity in erythema nodosum leprosum (ENL) (J. Sheskin, 1980, *The treatment of lepra reaction in lepromatous leprosy*, International Journal of Dermatology, 6:318-322) and in autoimmune disorders (E. Atra and E. I. Sato, 1993, Treatment of the cutaneous lesions of systemic lupus erythematosus with thalidomide. Clinical and Experimental Rheumatology, 11(5):487-93). Lenalidomide has been found to have anti-angiogenic properties and has emerged as a drug with activity against various hematological and solid malignancies such as myelodysplasia, multiple myeloma, chronic lymphocytic leukemia, primary systemic amyloidosis, non-Hodgkin's lymphoma, myelofibrosis with myeloid metaplasia and Waldenstrom Macroglobulinemia (Venumadhav Kotla, et al., 2009, *Mechanism of action of lenalidomide in hematological malignancies*, Journal of Hematology & Oncology, 2:36). The clinical evidence for therapeutic potential of Lenalidomide in various malignant conditions is consistent with the multitude of pharmacodynamic effects that have been shown in vitro and in animal models through various mechanisms in different hematologic malignancies. Lenalidomide can upregulate the tumor suppresser gene, p21; and thus, induce the apoptosis of cancer cells (Verhelle D., et al., 2007, *Lenalidomide and CC-4047 inhibit the proliferation of malignant B cells while expanding normal CD34$^+$ progenitor cells*. Cancer Res., 67(2):746-55). Lenalidomide have also been shown to significantly decrease the expression of angiogenic factors VEGF and Interleukin-6 (IL-6) in multiple myeloma; thereby reducing angiogenesis and hence contributing to clinical treatment activity in multiple myeloma (Gupta D., et al., 2001, *Adherence of multiple myeloma cells to bone marrow stromal cells upregulates vascular endothelial growth factor secretion: therapeutic applications*. Leukemia, 15(12): 1950-61).

The aim of the present invention is binding or conjugating HA with a drug aforesaid, with or without a linker or spacer, by carboxyl group, hydroxyl group, or amino group of HA to accomplish working effect on specific location and specific time. Therefore, HA as a target delivery vehicle to carry the drug to the specific site that has abundant CD44 can produce better treatment efficacy and safety.

As used herein, in general, the term "linker" or "spacer" means an organic moiety that connects two parts of a compound. Linkers typically comprise a direct bond or an atom such as oxygen or sulfur, a unit such as SS, NH, C(O), C(O)NH, SO, $SO_2$, $SO_2NH$ or a chain of atoms, such as substituted or unsubstituted alkyl where one or more methylenes can be interrupted or terminated by O, S, S(O), $SO_2$, NH, $NH_2$, C(O). The term "linker" or "spacer" of the present invention may be absent and denotes any chemical compound present between the drug and the HA which may be removed chemically, enzymatically or may decompose spontaneously; it also contains at least one other group useful for linking the drug, e.g. amino, thiol, further carboxy groups, etc. The linker or spacer may be a polypeptide, a peptide, or a lipid.

Suitable linkers or spacers are e.g. linear or branched, aliphatic, aromatic or araliphatic $C_2$-$C_{20}$ dicarboxylic acids, aminoacids, peptides.

The role of the linker, whenever present, consists in creating an arm or a spacer between the hyaluronic acid and the drug. The linker engages, on one side, the HA via the amide, carboxyl group, hydroxyl group, or amino group linkage and, on the other side, the drug via any possible covalent-type bond.

When the linker or spacer is a dicarboxylic acid, the carboxylic group forming the ester bond with the drug may be the hydroxyl group of the compound. When the linker or spacer is a dihydrazide, the amino group forming the amide bond with HA may be the free carboxylic group of the HA. Preferred linkers or spacers are: succinic acid to drug, adipic dihydrazide (ADH) to HA.

In the preferred embodiment, the present invention provides a compound consisting of a conjugate from a glycosaminoglycan, preferably hyaluronic acid, and an active compound, wherein the active compound is conjugated by means of a functional group to a carboxylic group of the glycosaminoglycan, its derivative, or a salt thereof to form a covalent conjugation, and wherein the active compound is selected from a group consisting of Lenalidomide, Gemcitabine, and a COX-2 antagonist.

The active compounds lenalidominde, Gemcitabine, or the preferred COX-2 antagonist Nimesulide or Celecoxib can be bound preferably directly by means the functional carboxylic group of the HA and the —$NH_2$ group of the active compounds.

In a preferred embodiment of the present invention, the covalent conjugation, either direct or indirect through a linker, between one of the functional carboxyl groups of HA and of the active compound can be either an amidic bond or an ester bond.

In case of indirect conjugation by means of a linker, said linkers are selected from a polypeptide, a peptide, a lipid, an aminoacid or a linear or branched, aliphatic, aromatic or araliphatic $C_2$-$C_{20}$ dicarboxylic acids.

The preferred HA for conjugation has an average molecular weight in the range comprised from 10 kDa to 2000 kDa and the conjugation involves at least 40% of the carboxyl group of HA.

The glycosaminoglycan conjugates according to the invention are preferably for use for treating cancer diseases and preferably in a most preferred embodiment of the present invention the cancer diseases are selected from liver cancer, hepatocellular carcinoma, cholangiocarcinoma, cholangiocellular cystadenocarcinoma, colon cancer, adenocarcinoma, lymphoma and squamous cell carcinoma, breast cancer, ductal carcinomas, lobular carcinomas, lung cancer, non-small-cell lung carcinoma, small-cell lung carcinoma, ovarian cancer, prostate cancer, renal cancer, renal cell carcinoma, urothelial cell carcinoma, multiple myeloma, myelodysplastic syndromes (MDS), Hodgkin's lymphoma, non-Hodgkin's lymphoma, chronic lymphocytic leukemia, or carcinoma of the pancreas.

Figure 3:
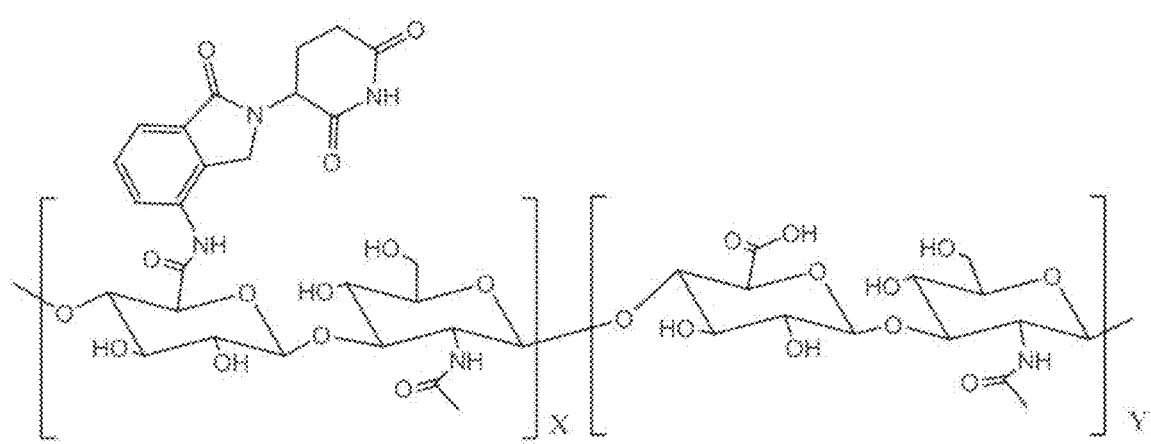
FIG. 3 shows the structure of HA-Lenalidomide conjugate.
Figure 5A:
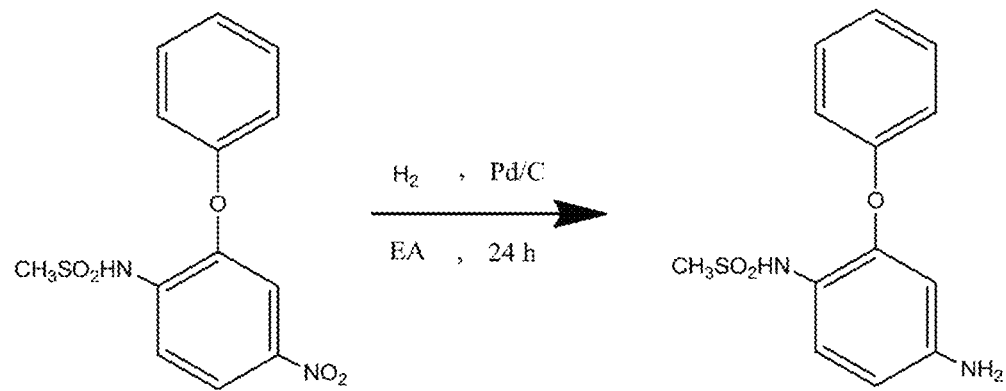
FIG. 5A shows the structure of genuine Nimesulide (having —$NO_2$ group, $NiNO_2$) and the hydrogenation modified production (having —$NH_2$ group, $NiNH_2$).
Figure 5B:
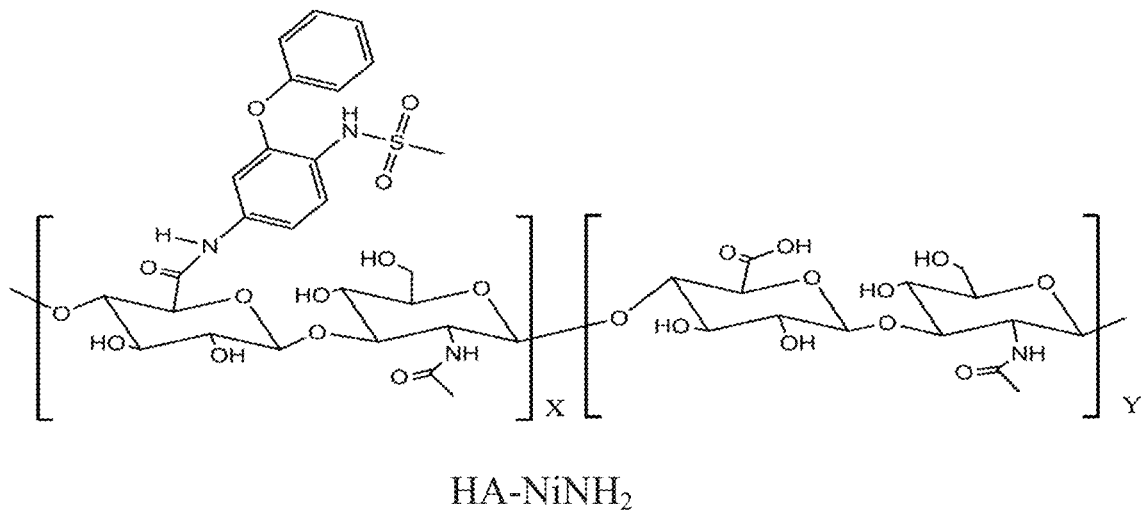
FIG. 5B shows the structure of HA-$NiNH_2$ conjugate.
Figure 8:
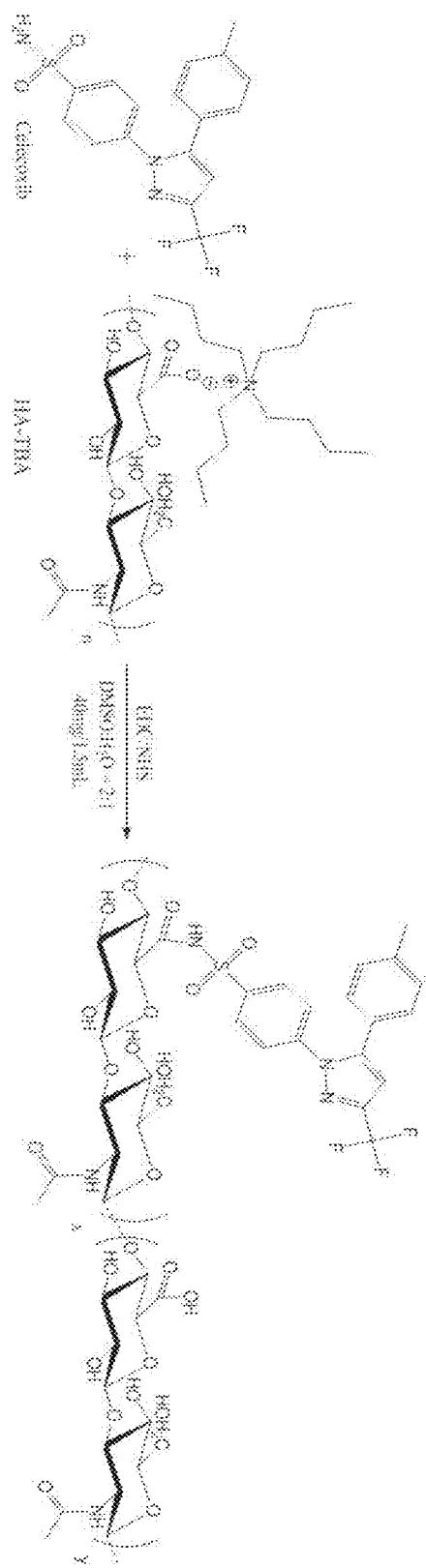
FIG. 8 shows the synthesis procedure and the structure of HA-Celecoxib.
Figure 10:
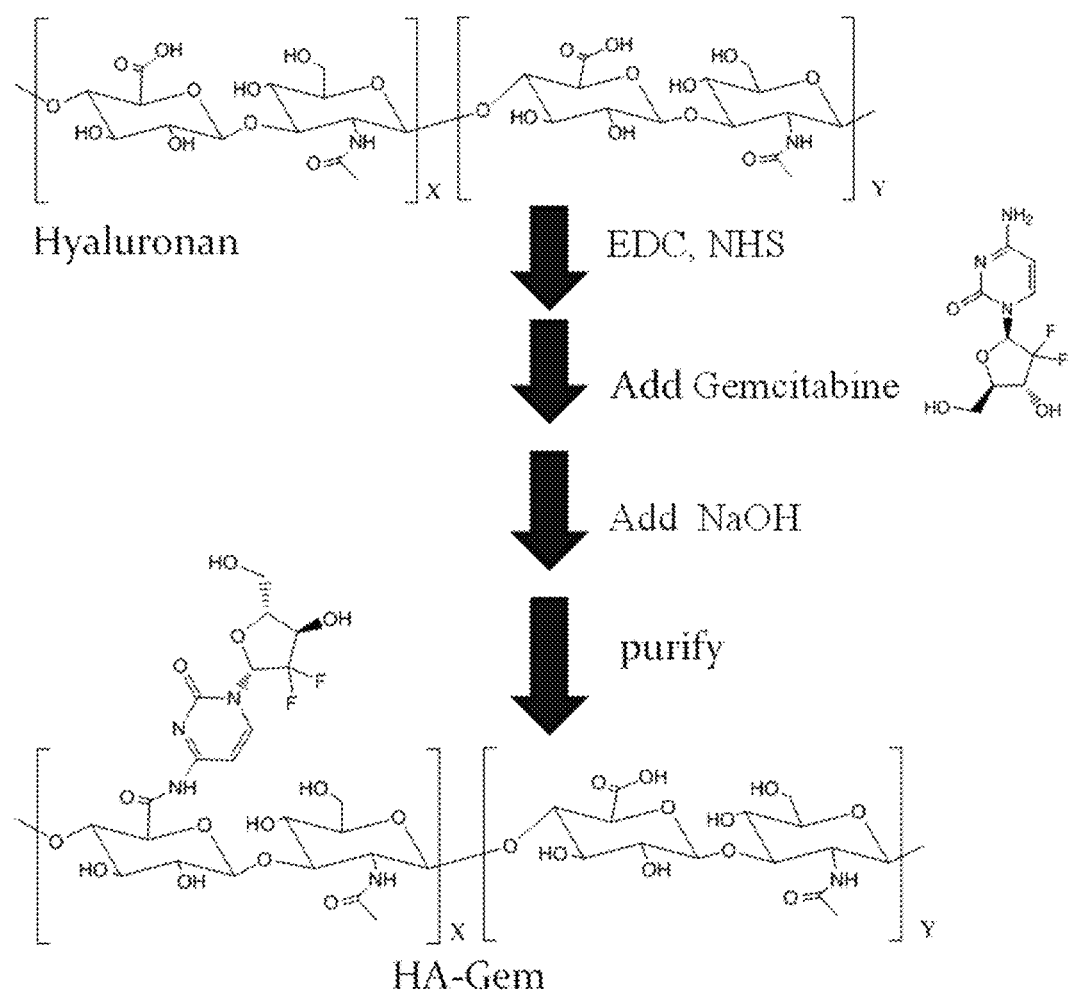
FIG. 10 shows the synthesis procedure and the structure of HA-Gemcitabine.

Therefore, the present invention provides anti-cancer drug conjugates of HA with Lenalidomide, HA with Gemcitabine, HA with Nimesulide, and HA with Celecoxib, where the Lenalidomide, Gemcitabine and Celecoxib are conjugated with HA by the formation of amide bond between the $-NH_2$ group of Lenalidomide and the $-COOH$ group of HA, respectively; furthermore, for the Nimesulide, the $-NO_2$ group has been modified to $-NH_2$ group so that the Nimesulide can covalently bind to $-COOH$ group of HA via an amide bond to form the HA-NiNH$_2$ conjugate. The structure of HA-Lenalidomide conjugate is shown in FIG. 3. The structures of genuine Nimesulide (NiNO$_2$) and the hydrogenation production, NiNH$_2$, are shown in FIG. 5A, and the structure of HA-NiNH$_2$ conjugate is shown in FIG. 5B. The structure of HA-Celecoxib conjugate is shown in FIG. 8. The structure of HA-Gemcitabine conjugate is shown in FIG. 10.

Figure 4A:
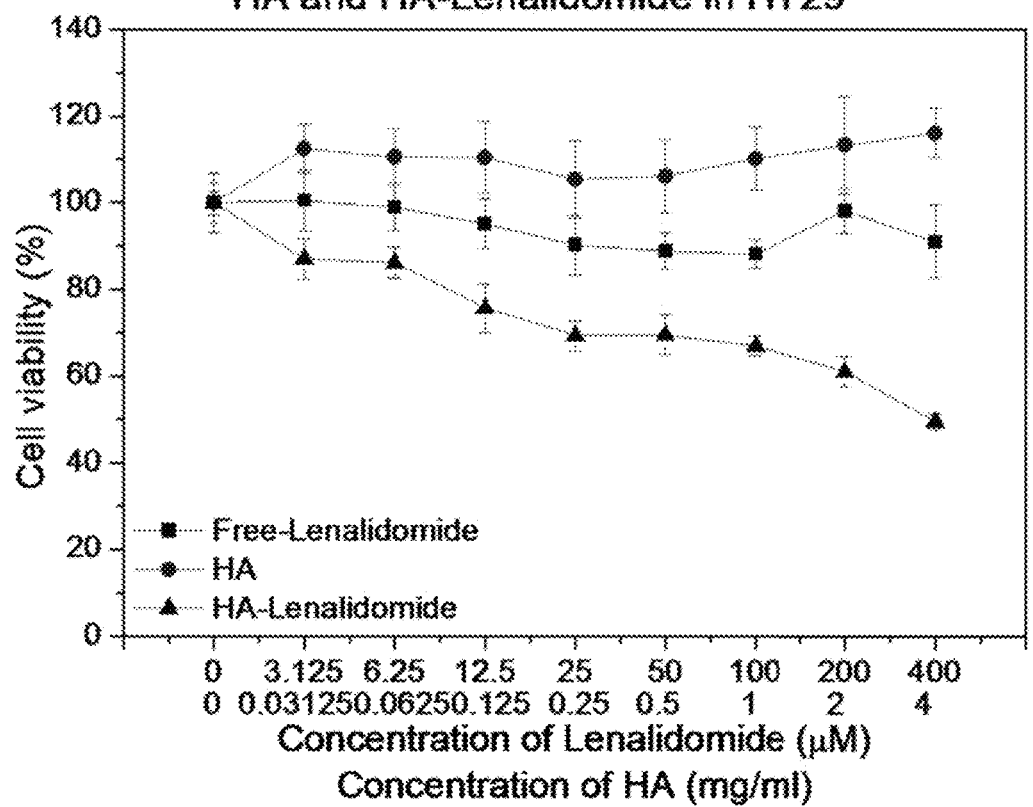
FIG. 4A shows the cytotoxicity effect of free Lenalidomide, HA, and HA-Lenalidomide conjugate on HT29 cell line.
Figure 4B:
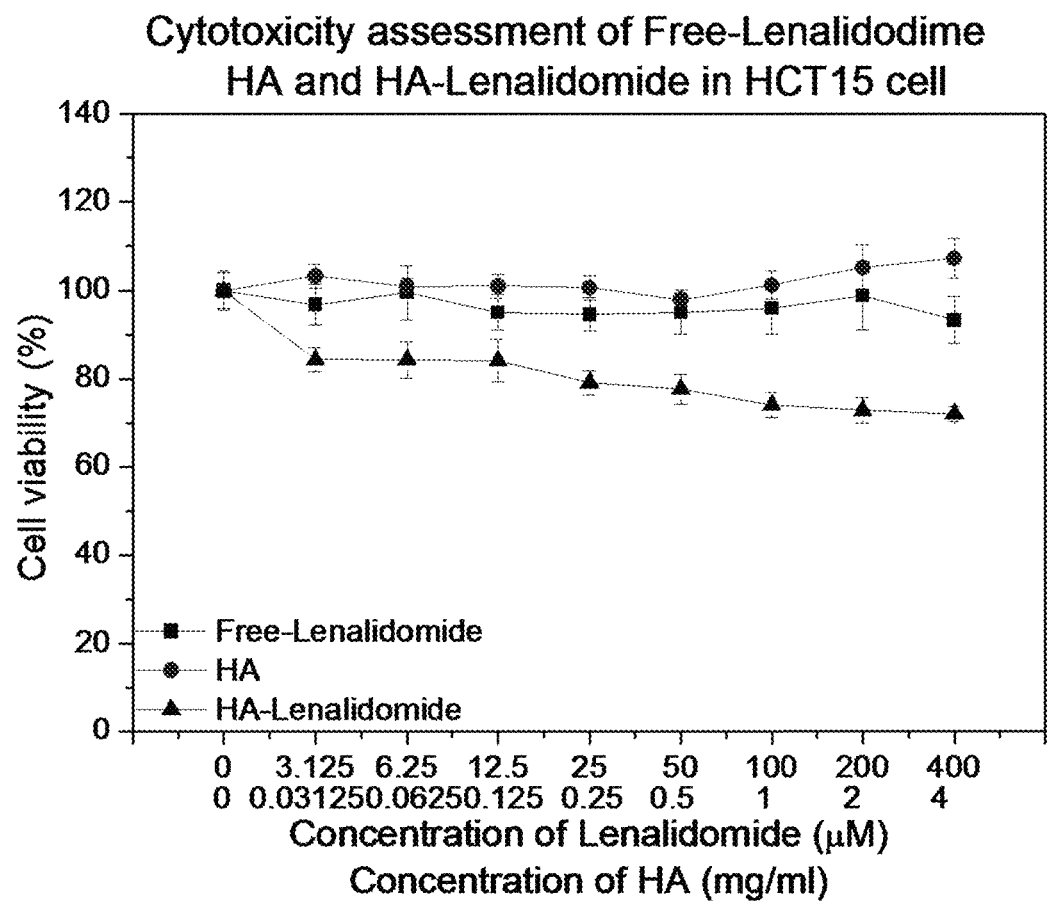
FIG. 4B shows the cytotoxicity effect of free Lenalidomide, HA, and HA-Lenalidomide conjugate on HCT15 cell line.

In an embodiment, the result of the present invention showed that in CD44 rich cell line (HT29), the HA-Lenalidomide conjugate exhibits significant cytotoxic effect than Lenalidomide or HA does respectively (FIG. 4A); nevertheless, this trend of synergistic effect was not so noticeable in cell line HCT15 (FIG. 4B). The result of the present invention shows that the trend of cell viability in HCT15 with less abundant CD44 is higher than in HT29 with abundant CD44 under HA-Lenalidomide treatment meaning that the CD44-rich cell line, HT29, is much sensitive to HA-Lenalidomide treatment; however, the effect of Lenalidomide on cell viability is almost the same in both cell lines. This result represents that Lenalidomide does not have interaction with CD44, and HA indeed can enhance the therapy efficacy of Lenalidomide while conjugated together comparing in the same drug amount.

Figure 6A:
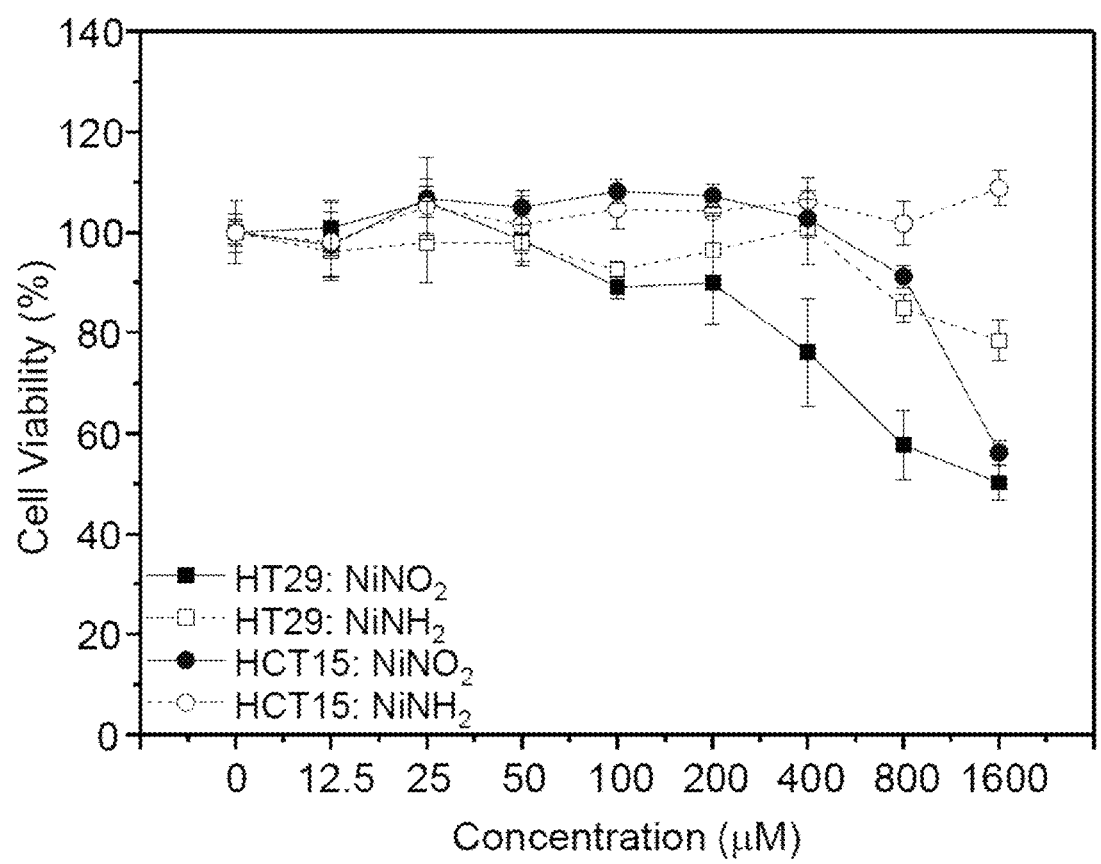
FIG. 6A shows the cytotoxicity effect of the $NiNO_2$ and $NiNH_2$ either in HT29 or HCT15.
Figure 6B:
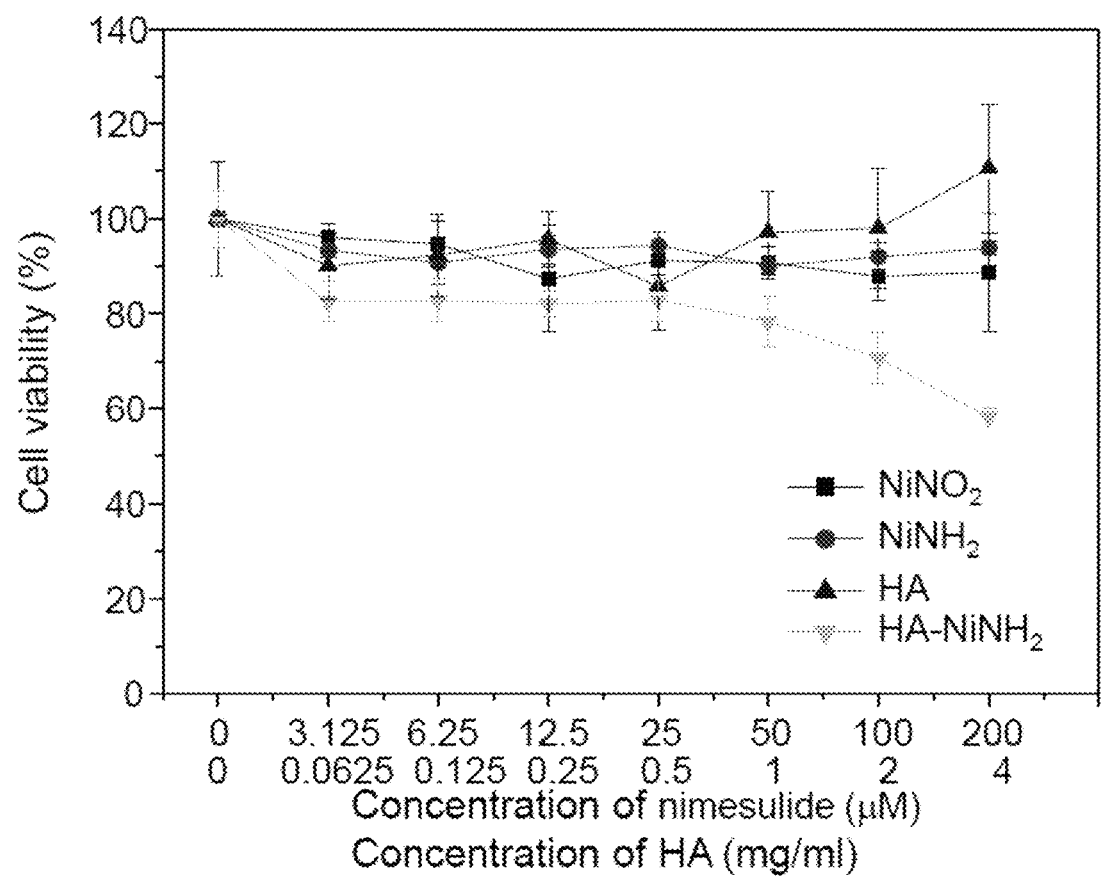
FIG. 6B shows the cytotoxicity effect of the $NiNO_2$, $NiNH_2$, HA, and HA-$NiNH_2$ conjugate in HT29.

In another embodiment, the result of the present invention showed that the cytotoxicity effect of the genuine Nimesulide (having nitro functional group, $-NO_2$) is generally better than that of hydrogenation modified production (having amine functional group, $-NH_2$) either in HT29 or HCT15 especially in higher dose (FIG. 6A). However, when NiNH$_2$ is conjugated with HA, the cytotoxicity of HA-NiNH$_2$ is significant over than that of either NiNH$_2$ or NiNO$_2$ alone (FIG. 6B). This result is all the same with the embodiment of HA conjugating with Lenalidomide. Therefore, the cytotoxicity effect of anticancer drugs could be enhanced by conjugating with HA.

Figure 7A:
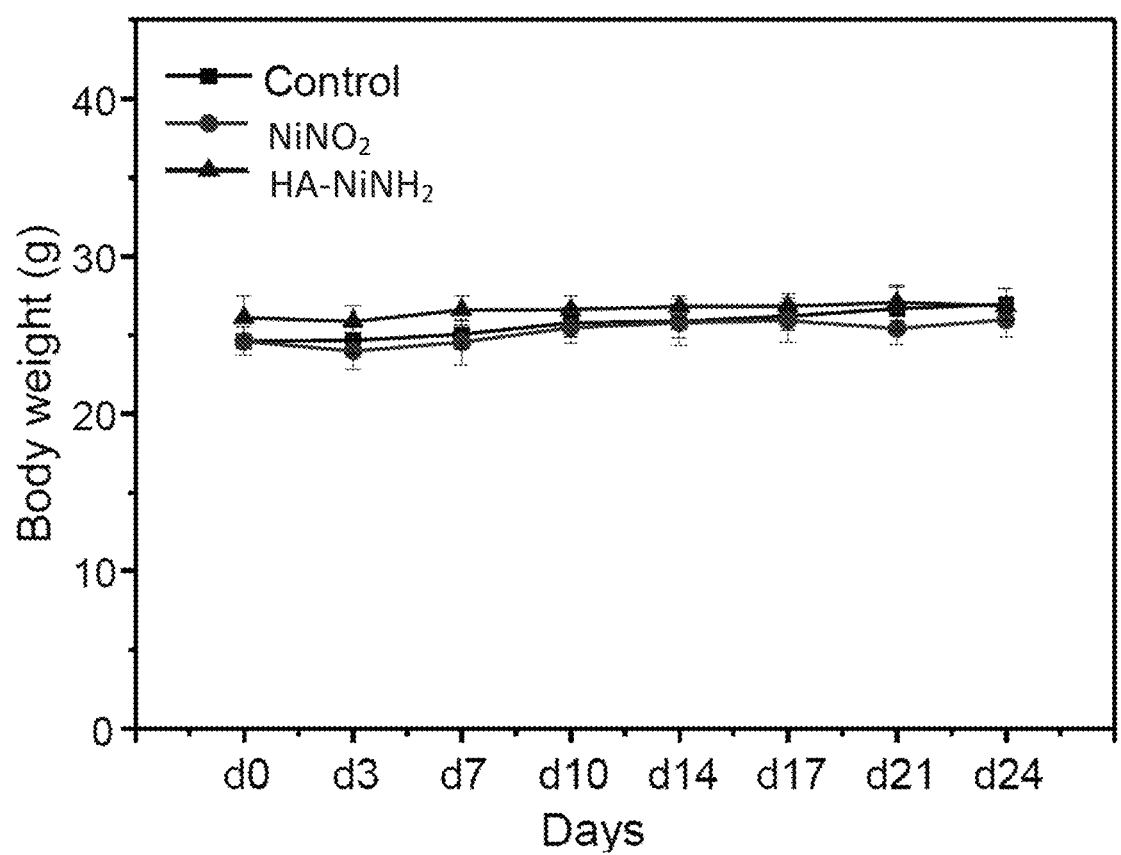
FIG. 7A shows the total body weights of mice of each of three groups within 24 days.
Figure 7B:
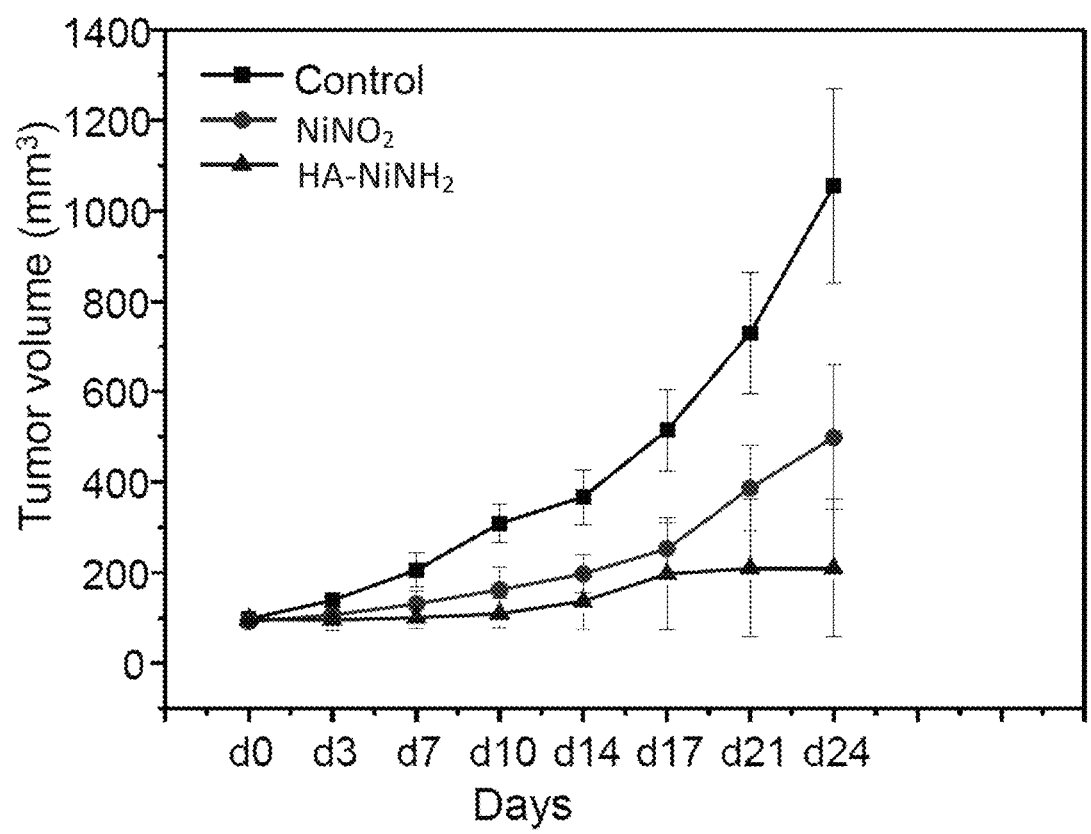
FIG. 7B shows tumor suppression effect by the groups of control, $NiNO_2$, and HA-$NiNH_2$.

Furthermore, in the embodiment of animal test, the result of the present invention shows that the tumor suppression effect of HA-NiNH$_2$ is more potent than that of NiNO$_2$ or control group (FIG. 7B). The result showed that average body weights of each mice of three groups were almost the same within 24 days (FIG. 7A) indicating there are no significant adverse effect such as weight loss; however, the tumor volume shown significantly different when comparing within each group of control, NiNO$_2$, and HA-NiNH$_2$, the HA-NiNH$_2$ group has better tumor suppression effect than either Nimesulide or control group does (FIG. 7B). This result indicates that the conjugate of HA-NiNH$_2$ of the present invention has superior treatment effect than NiNO$_2$ alone.

Figure 9A:
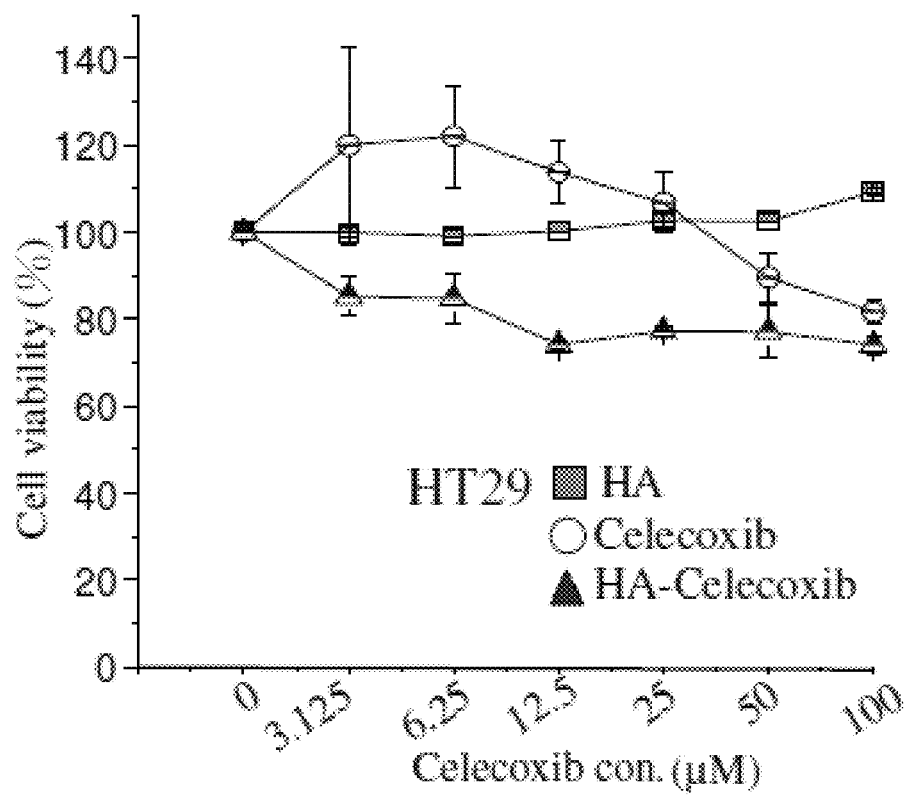
FIG. 9A shows the cytotoxicity effect of HA, Celecoxib, and HA-Celecoxib conjugate on HT29 cell line.
Figure 9B:
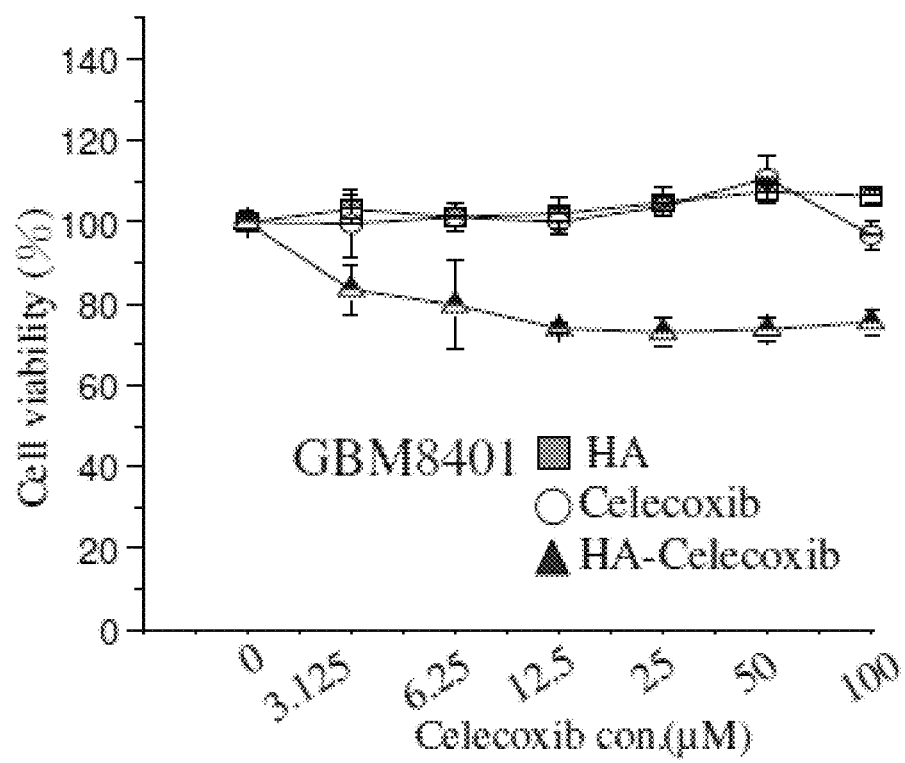
FIG. 9B shows the cytotoxicity effect of HA, Celecoxib, and HA-Celecoxib conjugate on GBM8401 cell line.
Figure 11:
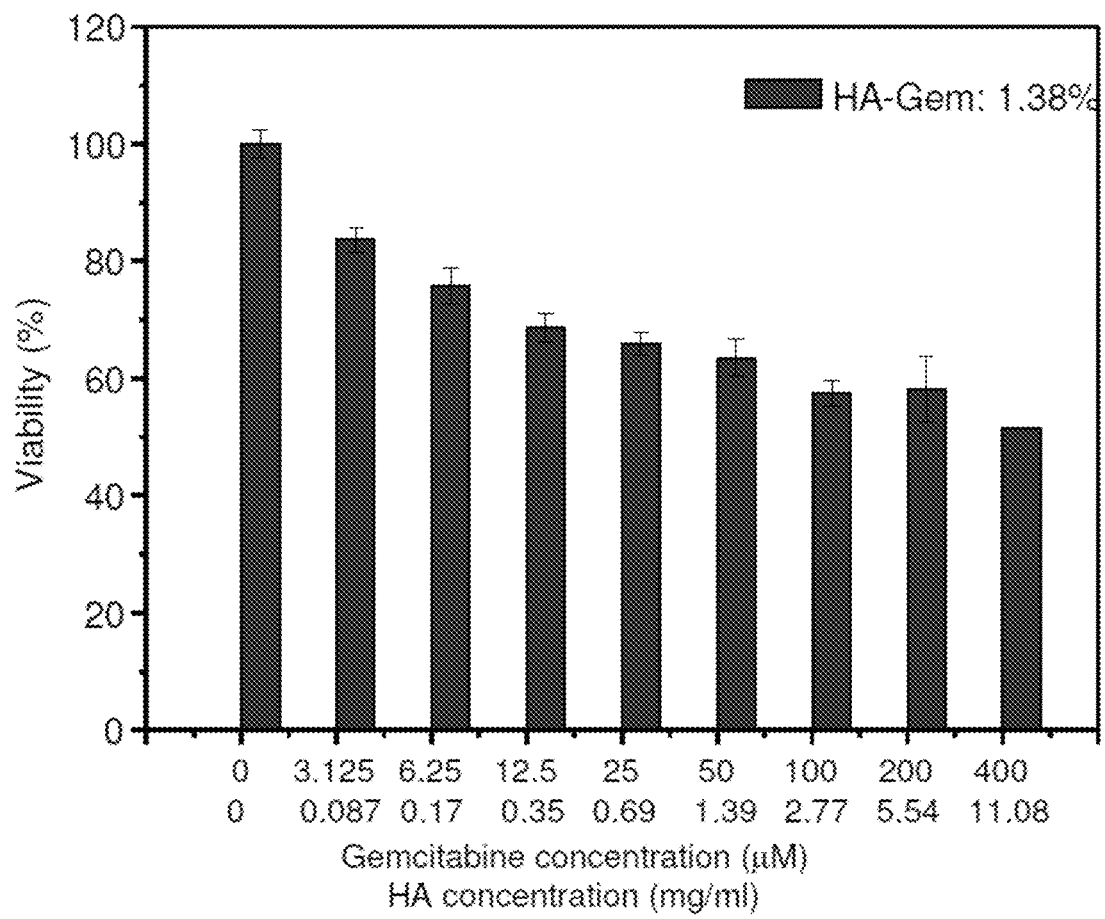
FIG. 11 shows the cytotoxicity effect of HA-Gemcitabine conjugate on A549 cell line.
Figure 12:
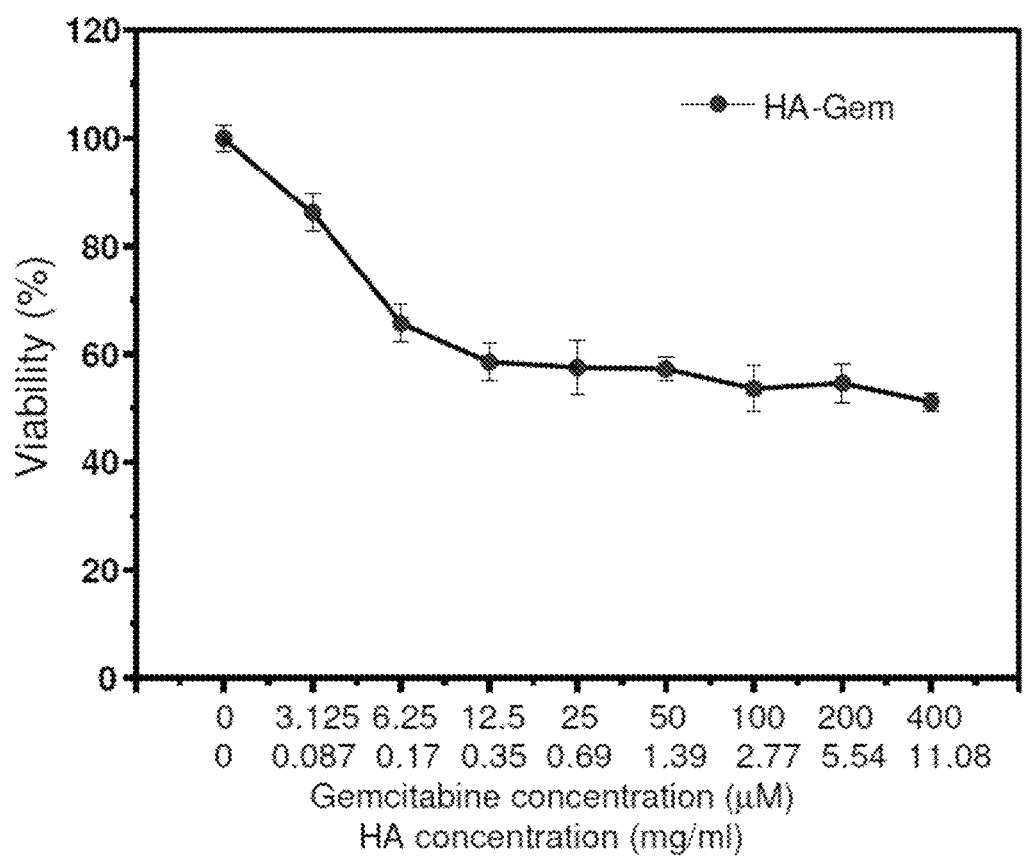
FIG. 12 shows the cytotoxicity effect of HA-Gemcitabine conjugate on GBM8401 cell line.

The result showed that the cytotoxicity effect of the HA-Celecoxib has a trend better than HA and Celecoxib along in HT29 cells and GBM8401 cells (FIGS. 9A and 9B). And the result showed a trend that the cytotoxicity effect of the HA-Gemcitabine has increased in A549 cells (FIG. 11) and GBM8401 cells (FIG. 12).

All together, the antitumor efficacy of Lenalidomide and Nimesulide conjugated with HA was compared with Lenalidomide and Nimesulide alone and respectively significantly improved cytotoxicity effect and tumor suppression efficacy. The results aforementioned show that the present invention has great contribution on enhancing the treatment effect of cancer drug including Lenalidomide and Nimesulide.

In order to treat the disease, the preferred embodiment of the formulation or dosage form of the present invention including an excipient to formulate an administrating dosage form for eye, ear, oral, nose, respiratory tract, gastrointestinal tract, circulation system or topical use. The more preferred embodiment of the oral dosage form is selected from the group consisting of solid dosage form, solution including, but not limited to suspension, tablet including, but not limited to controlled-release tablet, and capsule including, but not limited to enteric-coated capsule. The more preferred embodiment of the gastrointestinal tract administration form is selected from the group consisting of solid dosage form, perfusion, enema, suppository, and solution including, but not limited to, suspension. The more preferred embodiment of the circulation system or systemic administration form is selected from the group consisting of introvenous (IV), intra-muscle (IM) and subcutaneous (SC). The more preferred embodiment of the topical administration form is selected from the group consisting of perfusion, enema, suppository, spray, inhalation, and drop.

The method for preparing a compound consisting of a conjugate from a glycosaminoglycan and an active pharmaceutical compound object of the invention comprising the steps of:

preparing a water solution of a glycosaminoglycan, preferably hyaluronic acid;

preparing a water solution of Lenalidomide, Gemcitabine, or COX-2 antagonist with N-(3-Dimethylamino propyl)-N-ethyl carbodiimide hydrochloride and N-Hydroxysuccinimde;

mixing and stirring both of the solutions at room temperature for at least 10 hours to obtain a mixed solution; and dialyzing the mixed solution for several days.

The following examples are given for the purpose of illustrating various embodiments of the invention and are not meant to limit the present invention in any fashion.

EXAMPLE

Example 1

The Adhesion of HA in Colon Tissue (IVIS Image System-Vision 3)

Procedure:

1. 0.25 g high molecule weight sodium hyaluronate powder (HHA; Mw: 2 MDa; Freda) and 0.25 g low molecule weight sodium hyaluronate powder (LHA; Mw: 0.35 MDa; Freda) were added into 50 ml PBS buffer (Phosphate buffered saline) respectively to form 0.5% solution, and then stirred for 6 hours until the powder was totally dissolved. 0.25 g medium molecule weight sodium hyaluronate powder (MHA; Mw: 1 MDa; Freda) was added into 50 ml PBS buffer, and then stirred for 6 hours until the powder was totally dissolved and ready for use in the following steps.

2. Fluorescent HA (HA-f) was prepared by (1) 0.39 g MES free acid (2-(N-morpholino) ethanesulfonic acid, Calbiochem) and was dissolved in 100 ml dd water. (2) Solution A: 65 mg fluroresceinamine powder, (isomer I, Fluka) was dissolved in 9 ml 95% EtOH solution and then stirred for 10 minutes under a condition that light was prohibited. (3) Solution B: 359 mg EDC powder (N-(3-Dimethylamino propyl)-N-ethyl carbodiimide hydrochloride, Sigma) was dissolved in 9 ml MES buffer and then stirred for 10 minutes. (4) Solution C: 216 mg NHS powder (N-Hydroxysuccinimde, Sigma) was dissolved in 9 ml MES buffer and then stirred for 10 minutes. (5) 3 ml Solution A was slowly dropped into 50 ml 0.5% HA solution and then stirred for 10 minutes under a condition that light was prohibited. (6) 3 ml Solution B and 5 ml Solution C were separately dropped into the solution of step (5) and then stirred for 10 minutes under a condition that light was prohibited. (7) 0.02 M MES buffer was slowly added into the solution of step (6) until the volume reached 100 ml and was then stirred for 24 hours at room temperature under a condition that light was prohibited. (8) The product after reaction was poured into a dialysis tubing (MW: 1200~14000) in 5 L dd water as a dialysis solution and then stirred for 5 days at 4° C. under a condition that light was prohibited with dialysis solution being changed every 12 hours until the dialysis solution had no fluorescence. (9) The liquid after dialysis was allocated into 50 c.c. plastic centrifuge tubes and then reserved at −20° C. refrigerator overnight, followed by drying in a freeze-drying machine under a condition that light was prohibited. (10) The dried HA-f powder was reserved at −20° C. refrigerator. (11) 50 mg HA-f powder was slowly added into 10 ml PBS buffer and then stirred for 6 hours until the powder was totally dissolved.

3. Colon tissue of SD-rat (Sprague-Dawley Rat) aged 7-8 weeks was cut by scalpel and then washed by PBS buffer, followed by being cut to 3-4 cm long with soaking in PBS buffer finally.

4. Injured colon tissue was prepared by brushing by toothbrush for 20 times longitudinally and then soaking in PBS buffer.

5. Normal and injured colon tissues were put into a 12-well plate and then 1 ml 0.5% HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times.

6. Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.

7. All values are calculated as means of n observations. The histological index was analyzed by Student's t-test.

Result: The fluorescent index was quantified and arranged as in FIG. 1. The fluorescent index of normal colon tissue was defined as 1. The other colon tissues tests were calibrated by the defined value. The result showed that the HAs with the same average Mw were adhered in the injured colon tissues with obviously higher fluorescent index than in the normal colon tissues (P<0.01). Comparing the difference between HAs of three different average molecular weights adhered in the injured colon tissues, the fluorescent index of adhesion of 350 KDa HA by the injured colon tissues was obviously higher than HAs of the other two average molecular weights (2 MDa and 1 MDa). Further, the fluorescent index of adhesion of 1 MDa HA by even normal or injured colon tissues was higher than 2 MDa HA.

Example 2

HA-Dye Conjugation Process and HA-Dye In Vitro Image

1. The following whole process of HA-dye conjugation must be kept in dark.

The Synthesis of HA-ADH

1. HA (0.34 MDa, 50 mg) was dissolved in water to give a concentration of 4 mg/ml.

2. 5-fold excess (114.8 mg) of ADH was added into the solution.

3. The pH of the reaction mixture was adjusted to 4.75 by addition of 0.1 N HCl.

4. Next, 1 equiv. (25.1 mg) of EDC was added in solid form. The pH of the reaction mixture was maintained at 4.75 by addition of 0.1 N HCl.

5. After 15 minutes reacting, the reaction was quenched by addition of 0.1 N NaOH to adjust the pH of reaction mixture to 7.0.

6. The reaction mixture was then transferred to pretreated dialysis tubing (Mw cutoff 3500) and dialyzed exhaustively against 100 mM NaCl, then 25% EtOH/water 4 cycles and finally water. The solution was then filtered through 0.2 μm cellulose acetate membrane, flash frozen, and lyophilized.

7. The substitution degree of ADH was measured by 1H NMR.

The Synthesis of HA-ADH-FITC

1. HA-ADH (DS=36%) 88 mg was dissolved in 35 ml water

2. FITC 9.5 mg was dissolved in 10 ml DMSO.

3. Mix HA-ADH solution and FITC solution

4. After stirred 48 h at room temperature, the solution was dialyzed 3 days with 0.3 M NaCl and pure water alternately using MWCO 12000-14000 dialysis bag.

5. The solution was then freeze-drying 2 days.

6. Finally the degree of substitution by prednisolone was determined by UV spectrum.

HA-Dye In Vitro Image (1) $1 \times 10^5$ HT 29 cells and HCT15 cells (human colon carcinoma, a CD44 positive cell) were seeded onto a microscope slide in a 3.5 cm dish.

(2) Indicated dye concentrations, 1 μM of HA-dye (HA: 0.34 MDa) were added into cells for indicated time respectively.

(3) After incubation, cells were washed in PBS, and then fixed in 3.7% formaldehyde.

(4) Observation of the interaction between HA-dye and cells was performed by confocal microscopy.

Result: The fluorescent view can show the attachment site and amount of dye on HCT15 (FIG. 2A and FIG. 2B) and HT29 (FIG. 2C and FIG. 2D). The results reveal that dye has been successfully conjugated with HA and HA enhances HA-dye concentration on CD44 abundant site on HT29, whereas HT29 has stronger fluorescence that meets with more abundant CD44 than HCT15 has. Even proved that HA-dye can enter the cells (FIG. 2D). The HA-dye was accumulated after a 6 hrs treatment and internalized after a 12 hrs treatment in HT29 (+). Such phenomenon were not observed in HCT15 (less CD44) after a 6 hr or a 12 hr treatment of HA-dye.

Example 3

Cell Line and Xenograft Tumor Model

1. Cell Culture Condition and Passage
(1) Cell Culture Condition:
HT29: high glucose DMEM, 10% FBS, 1% sodium pyruvate, 1% Penicillin, Streptomycin, and Neomycin.
HCT15: DMEM/F12, 10% FBS, 1% sodium pyruvate, 1% Penicillin, Streptomycin, and Neomycin.
(2) Passage:
(I) Remove and discard culture medium.
(II) Briefly rinse the cell layer with 1×PBS to remove all traces of serum which contains trypsin inhibitor.
(III) Add 1 mL of 0.25% Trypsin-EDTA solution to flask and observe cells under the microscope until cell layer is dispersed (usually within 5 to 15 minutes). Then, add 9 mL of complete growth medium and aspirate cells by gently pipetting.
(IV) Add appropriate aliquots of the cell suspension to new culture dish. (subcultivation ratio of 1:3 to 1:8)
(V) Incubate cultures at 37° C. incubator (5% $CO_2$).
2. Xenograft Tumor Model
(1) HT29 and HCT 15 cells ($2×10^7$ cells/mice) were subcutaneously injected into the right and left hips separately (upper side of right and left hind legs) of eight weeks old male nude mice.
(2) IVIS experiment could begin to be conducted when the size of the xenograft tumors was within 400~500 $mm^3$ after 3-4 weeks.
3. IVIS Experiment
(1) After being anesthetized by isoflurane, the image of the xenograft nude mice was taken as a blank in the parameters of f/stop: 8, exposure time of 3 sec, excitation wavelength of 633 or 635 nm, and the measurement of emission wavelength of 668 nm. The instrument used was Xenogen IVIS 200.
(2) 200 µl of 12.5 µM Free-dye or 200 µl HA-dye solution having 12.5 µM dye of HA-dye with 0.1 mg HA (HA: 1.12 MDa) were injected intravenously via the tail vein respectively.
(3) Photos of IVIS image were taken after a predetermined time of 5, 10, 30 minutes and 1, 2 hours. The parameters of observation and the instrument were briefly described in step 1. Mice were sacrificed following dissection after 2 hours of injection to analyze the fluorescent distribution in viscera.

Result: The fluorescent image showed that free dye was almost evenly distributed in HT29 and HCT 15 (data not shown). The ratio of attachment area of HT29 is 50.15%, whereas HCT15 is 49.86%. However, HA-dye can especially attach more on CD44 abundant site of HT29 than HCT15, which has less CD44 than HT29 has. The ratio of attachment area of HT29 is 74.15%, whereas HCT15 is 25.85%. The result proved that HA can contribute to dye accumulation on CD44 abundant site.

Example 4

Synthesis of HA-Lenalidomide Conjugate

Procedure
1. 50 mg HA (10K-700 KDa) were dissolved in 25 ml D.D water.
2. EDC 25.1 mg and NHS 15.1 mg were mixed in 2 ml D.D water and stirred at room temperature for 5 minutes.
3. An HA solution was neutralized by adding 1.31 ml NaOH.
4. Lenalidomide 3.4 mg was dissolved in 2 ml dimethylsulfoxide (DMSO) solution.
5. This mixture (HA, EDC, NHS and Lenalidomide) was stirred at room temperature for 12 hours.
6. The mixture was dialyzed for 2~3 days against an excess of D.D water by using dialyzer bag (MWCO: 3500).
Result: FIG. 3 shows the structure of HA-Lenalidomide conjugate.

Example 5

In Vitro Cytotoxicity of Lenalidomide

Procedure
1. HT29 cells were seeded at low density of $1×10^4$ cells per well in 96 well-plates in medium containing high glucose DMEM, 10% FBS, 1% sodium pyruvate, 1% Penicillin, Streptomycin, and Neomycin.
2. HCT15 cells were seeded at low density of $1×10^4$ cells per well in 96 well-plates in medium containing DMEM/F12, 10% FBS, 1% sodium pyruvate, 1% Penicillin, Streptomycin, and Neomycin.
3. One day (24 hours) after seeding, cells were incubated in media containing indicated doses of following drugs-Lenalidomide: 400 µM, 200 µM, 100 µM, 50 µM, 25 µM, 12.5 µM, 6.25 µM, 3.125 µM and 0; HA: 4 mg/ml, 2 mg/ml, 1 mg/ml, 0.5 mg/ml, 0.25 mg/ml, 0.0625 mg/ml, 0.3125 mg/ml and 0; HA-Lenalidomide: 400 µM, 200 µM, 100 µM, 50 µM, 25 µM, 12.5 µM, 6.25 µM, 3.125 µM and 0 for 24 hours.
4. Drug effect on cellular viability was evaluated using an assay based on the cleavage of the yellow dye 3-(4,5-dimethyl-2-thiazolyl)-2, 5-diphenyl-2H-tetrazolium bromide (MTT) to purple formazan crystals by dehydrogenase activity in mitochondria.
5. After drug treatment for 24 hours, medium was removed and cell layers were rinsed with medium following MTT diluted (0.5 mg/ml) in medium for 4 hours at 37° C. incubator (5% $CO_2$).
6. The cells were then added with 100 µl/well DMSO and the optical density of the cellular homogenate was measured at 570 nm using ELISA reader.
7. The fraction of live cells was calculated by dividing the mean optical density obtained from treated cells by the mean optical density from untreated control cells.

Result: The result showed that in CD44 rich cell line (HT29) the HA-Lenalidomide conjugate has the effect to kill cell than Lenalidomide or HA alone (FIG. 4A). Similarly, this trend of synergistic effect was also found in cell line HCT15 (FIG. 4B).

Example 6

Synthesis of HA-$NiNH_2$ Conjugate

Hydrogenation of $NiNO_2$
1. 500 mg Nimesulide ($NiNO_2$) was totally solved in 20 ml ethyl acetate and then 200 mg 5% Pd/C (Palladium on carbon) as catalyst was added into the solution. Extracted the air from the bottle under continued stir and the air was replaced by $H_2$ gas up to 1 atm following stirring for 24 hours.
2. Thin layer chromatography (TLC silica gel slide 60 F254) was performed for the identification of the purity of the hydrogenation product with wavelength at 254 nm where the mobile phase was Hexane:Ethyl acetate=2:1.

3. After the identification of the product, the Pd/C was removed by filtration following rotary evaporator to remove the residual solvent.

4. The hydrogenation product was dissolved in solution of Hexane:Ethyl acetate=1:1 solution for further purification.

5. Silica gel column was used for the purification and eluted with elution solution (Hexane:Ethyl acetate=1:1).

6. The fraction with color was collected and the determinations of the concentration the structure were performed by UV and NMR respectively to confirm the yield of the hydrogenation product, $NiNH_2$.

7. The $NiNH_2$ powder was acquired by freeze dryer.

Synthesis of HA-$NiNH_2$ Conjugate 1. 50 mg HA (10-700 KDa) was dissolved in 25 ml DD water.

2. EDC 25.1 mg and NHS 15.1 mg were mixed in 1 ml DD water and stirred at room temperature for 5 minutes.

3. $NiNO_2$ 3.65 mg was dissolved in 1 ml DMSO solution and then slowly dropped into HA/EDC/NHS solution by syringe within 3 minutes.

4. This mixture (HA, EDC, NHS and $NiNH_2$) was stirred at room temperature for 12 hours in the dark.

5. The mixture was dialyzed for 2-3 days against an excess of DD water by using dialyzer bag (MWCO: 3500).

6. HA-$NiNH_2$ powder was acquired by dehydration through freeze dryer from HA-$NiNH_2$ solution.

Result: FIG. 5A shows the structure of genuine Nimesulide ($NiNO_2$) and the production $NiNH_2$. FIG. 5B shows the structure of HA-$NiNH_2$ conjugate.

Example 7

In Vitro Cytotoxicity of $NiNO_2$

Procedure

1. HT29 cells were seeded at low density of $1\times10^4$ cells per well in 96 well-plates in medium containing high glucose DMEM, 10% FBS, 1% sodium pyruvate, 1% Penicillin, Streptomycin, and Neomycin.

2. HCT15 cells were seeded at low density of $1\times10^4$ cells per well in 96 well-plates in medium containing DMEM/F12, 10% FBS, 1% sodium pyruvate, 1% Penicillin, Streptomycin, and Neomycin.

3. One day (24 hours) after seeding, cells were incubated in media containing indicated doses of following drugs—$NiNO_2$ (stands for Nimesulide having $NO_2$ group): 200 µM, 100 µM, 50 µM, 25 µM, 12.5 µM, 6.25 µM, 3.125 µM and 0; $NiNH_2$ (stands for Nimesulide having $NH_2$ group): 200 µM, 100 µM, 50 µM, 25 µM, 12.5 µM, 6.25 µM, 3.125 µM and 0; HA: 4 mg/ml, 2 mg/ml, 1 mg/ml, 0.5 mg/ml, 0.25 mg/ml, 0.0625 mg/ml, 0.3125 mg/ml and 0; HA-$NiNH_2$: 200 µM, 100 µM, 50 µM, 25 µM, 12.5 µM, 6.25 µM, 3.125 µM and 0 for 24 hours.

4. Drug effect on cellular viability was evaluated using an assay based on the cleavage of the yellow dye 3-(4,5-dimethyl-2-thiazolyl)-2,5-diphenyl-2H-tetrazolium bromide (MTT) to purple formazan crystals by dehydrogenase activity in mitochondria.

5. After drug treatment for 24 hr, medium was removed and cell layers were rinsed with medium following MTT diluted (0.5 mg/ml) in medium for 4 hours at 37° C. incubator (5% $CO_2$).

6. The cells were then added with 100 µl/well DMSO and the optical density of the cellular homogenate was measured at 570 nm using ELISA reader.

7. The fraction of live cells was calculated by dividing the mean optical density obtained from treated cells by the mean optical density from untreated control cells.

Result: The result showed that the cytotoxicity effect of the genuine Nimesulide (having $NO_2$ group) is generally better than modified production (having $NH_2$ group) either in HT29 or HCT15 (FIG. 6A). However, when Nimesulide is conjugated with HA, the cytotoxicity of HA-$NiNH_2$ is significant over than either $NiNH_2$ or $NiNO_2$ alone (FIG. 6B).

Example 8

Tumor Growth Inhibition in Xenograft Nude Mice Model Procedure

1. HT29 ($2\times10^7$ cells/mice) were subcutaneously injected into right hip (upper side of right legs) of eight weeks old female BALB/c athymic ($nu^+/nu^+$) mice.

2. Tumor growth inhibition experiment could begin to conduct when the size of the xenograft tumors was small than 100 $mm^3$ which was designated day 0.

3. Tumor sizes and body weight were measured every 3 or 5 days for the duration of the experiment.

4. Tumor volume was calculated as $½(4\pi/3)(L/2)(W/2)H$; where L is the length, W is the width, and H is the height of the tumor.

5. Mice were divided into different groups for the treatments of PBS-control, Nimesulide, or HA-Nimesulide.

6. Mice were administered via tail vein injections at doses of Nimesulide (1.5 mg/kg), HA-Nimesulide (equivalent to 1.5 mg/kg of Nimesulide) or PBS respectively with an interval of 48 or 72 hours.

7. The tumor size and change in body weight of each mouse were recorded.

Result: The result showed that the average body weight of each mouse was almost the same (FIG. 7A); however, when comparing with each group of control, $NiNO_2$, and HA-$NiNH_2$, the tumor volume was shown significantly different where the HA-$NiNH_2$ group has better tumor suppression effect than Nimesulide group and control (FIG. 7B). The result indicates that the conjugate of HA-$NiNH_2$, of the present invention has superior treatment effect than $NiNO_2$ alone.

Example 9

Synthesis of HA-Celecoxib Conjugate

Procedure 1. 100 mg HA (10K-700 KDa) were dissolved in 25 ml DD water.

2. Tetrabutylammonium hydroxide (TBA-OH) 0.8 eq was added into HA solution and stirred for 16 hours.

3. Dried the solution and the HA-TBA white solid was acquired.

4. HA-TBA 40 mg was dissolved in 1 ml DD water and then EDC 30 mg and NHS powder 18 mg were added into the solution and stirred at room temperature for 5 minutes.

5. Celecoxib 4 mg was dissolved in 2 ml dimethylsulfoxide (DMSO) solution.

6. This mixture (HA-TBA, EDC, NHS and Celecoxib) was stirred at room temperature for 72 hours.

7. The mixture was dialyzed for 1 day against that a ratio of DMSO and DD water is 2 to 1 by using dialyzer bag (MWCO: 1200~1400) and changed the solution three times.

8. The mixture was then dialyzed for 2 days against 0.3 M NaCl by using dialyzer bag (MWCO: 1200~1400) and changed the solution two times a day.

9. HA-Celecoxib powder was acquired by dehydration through freeze dryer from HA-Celecoxib solution.

Result: FIG. 8 shows the synthesis procedure and the structure of HA-Celecoxib conjugate.

Example 10

In Vitro Cytotoxicity of Celecoxib

Procedure

1. HT29 cells were seeded at low density of $1 \times 10^4$ cells per well in 96 well-plates in medium containing high glucose DMEM, 10% FBS, 1% sodium pyruvate, 1% Penicillin, Streptomycin, and Neomycin.

2. GBM8401 cells were seeded at low density of $1 \times 10^4$ cells per well in 96 well-plates in medium containing DMEM, 10% FBS, 1% sodium pyruvate, 1% Penicillin, Streptomycin, and Neomycin.

3. One day (24 hours) after seeding, cells were incubated in media containing indicated doses of following drugs HA-Celecoxib: 100 μM, 50 μM, 25 μM, 12.5 μM, 6.25 μM, 3.125 μM and 0; for 24 hours.

4. Drug effect on cellular viability was evaluated using an assay based on the cleavage of the yellow dye 3-(4,5-dimethyl-2-thiazolyl)-2,5-diphenyl-2H-tetrazolium bromide (MTT) to purple formazan crystals by dehydrogenase activity in mitochondria.

5. After drug treatment for 24 hr, medium was removed and cell layers were rinsed with medium following MTT diluted (0.5 mg/ml) in medium for 4 hours at 37° C. incubator (5% $CO_2$).

6. The cells were then added with 100 μl/well DMSO and the optical density of the cellular homogenate was measured at 570 nm using ELISA reader.

7. The fraction of live cells was calculated by dividing the mean optical density obtained from treated cells by the mean optical density from untreated control cells.

Result: The result showed that the cytotoxicity effect of the HA-Celecoxib has a trend better than HA and Celecoxib along in HT29 cells and GBM8401 cells (FIG. 9A and FIG. 9B).

Example 11

Synthesis of HA-Gemcitabine Conjugate

Procedure 1. 50 mg HA (10-700 KDa) was dissolved in 25 ml DD water.

2. EDC 25.1 mg and NHS 15.1 mg were mixed in 1 ml DD water and stirred at room temperature for 5 minutes.

3. HA solution was neutralized by adding 1.44 ml NaOH.

4. Gemcitabine 3.9 mg was dissolved in 1 ml D.D water with 1 ml DMSO solution and then slowly dropped into HA/EDC/NHS solution by syringe within 3 minutes.

5. This mixture (HA, EDC, NHS and Gemcitabine) was stirred at room temperature for 12 hours in the dark.

6. The mixture was dialyzed for 2-3 days against an excess of DD water by using dialyzer bag (MWCO: 12000~14000).

7. HA-Gemcitabine powder was acquired by dehydration through freeze dryer from HA-Gemcitabine solution.

Result: FIG. 10 shows the synthesis procedure and the structure of HA-Gemcitabine conjugate.

Example 12

In Vitro Cytotoxicity of Gemcitabine

Procedure

1. A549 cells were seeded at low density of $1 \times 10^4$ cells per well in 96 well-plates in medium containing high glucose DMEM, 10% FBS, 1% sodium pyruvate, 1% Penicillin, Streptomycin, and Neomycin.

2. GBM8401 cells were seeded at low density of $1 \times 10^4$ cells per well in 96 well-plates in medium containing DMEM, 10% FBS, 1% sodium pyruvate, 1% Penicillin, Streptomycin, and Neomycin.

3. One day (24 hours) after seeding, cells were incubated in media containing indicated doses of following drugs—HA-gem: 400 μM, 200 μM, 100 μM, 50 μM, 25 μM, 12.5 μM, 6.25 μM, 3.125 μM and 0; for 48 hours.

4. One day (24 hours) after seeding, cells were incubated in media containing indicated doses of following drugs—HA-Celecoxib: 200 μM, 100 μM, 50 μM, 25 μM, 12.5 μM, 6.25 μM, 3.125 μM and 0; for 24 hours.

5. Drug effect on cellular viability was evaluated using an assay based on the cleavage of the yellow dye 3-(4,5-dimethyl-2-thiazolyl)-2,5-diphenyl-2H-tetrazolium bromide (MTT) to purple formazan crystals by dehydrogenase activity in mitochondria.

6. After drug treatment for 24 hr, medium was removed and cell layers were rinsed with medium following MTT diluted (0.5 mg/ml) in medium for 4 hours at 37° C. incubator (5% $CO_2$).

7. The cells were then added with 100 μl/well DMSO and the optical density of the cellular homogenate was measured at 570 nm using ELISA reader.

8. The fraction of live cells was calculated by dividing the mean optical density obtained from treated cells by the mean optical density from untreated control cells.

Result: The result showed a trend that the cytotoxicity effect of the HA-Gemcitabine has increased in A549 cells (FIG. 11) and GBM8401 cells (FIG. 12).

What is claimed is:

1. A compound consisting of a conjugate from a hyaluronic acid and an active compound, wherein the active compound is conjugated by means of a functional group to a carboxylic group of the hyaluronic acid, or a salt thereof to form a covalent conjugate, and wherein the active compound is selected from a group consisting of Lenalidomide, Nimesulide and Celecoxib; wherein the covalent conjugation is a direct conjugation by means of an amide bond.

2. The compound according to claim 1, wherein the hyaluronic acid has an average molecular weight comprised in the range from 10 kDa to 2000 kDa.

3. The compound according to claim 1, for use in the treatment of colon cancer, or glioblastoma.

4. A pharmaceutical composition comprising at least one conjugate from a hyaluronic acid and an active compound according to claim 1 in combination with at least one excipient and/or diluent.

5. The pharmaceutical composition according to claim 4, wherein the composition is for treating colon cancer, or glioblastoma.

* * * * *